(12) United States Patent
Yura et al.

(10) Patent No.: US 7,612,113 B2
(45) Date of Patent: *Nov. 3, 2009

(54) HYDROXY TETRAHYDRO-NAPHTHALENYLUREA DERIVATIVES

(75) Inventors: Takeshi Yura, Aichi-ken (JP); Muneto Mogi, Nara-ken (JP); Klaus Urbahns, Lund (SE); Hiroshi Fujishima, Nara-ken (JP); Tsutomu Masuda, Aichi-ken (JP); Toshiya Moriwaki, Nara-ken (JP); Nagahiro Yoshida, Kyoto-fu (JP); Toshio Kokubo, Nara-ken (JP); Masahiro Shiroo, Teversham (GB); Masaomi Tajimi, Aichi-ken (JP); Yasuhiro Tsukimi, Hyogo-ken (JP); Noriyuki Yamamoto, Osaka-fu (JP)

(73) Assignee: Xention Limited, Cambridgeshire (GB)

( * ) Notice: Subject to any disclaimer, the term of this patent is extended or adjusted under 35 U.S.C. 154(b) by 429 days.

This patent is subject to a terminal disclaimer.

(21) Appl. No.: 10/513,848

(22) PCT Filed: Apr. 28, 2003

(86) PCT No.: PCT/EP03/04395

§ 371 (c)(1),
(2), (4) Date: Jun. 2, 2006

(87) PCT Pub. No.: WO03/095420

PCT Pub. Date: Nov. 20, 2003

(65) Prior Publication Data

US 2006/0258742 A1    Nov. 16, 2006

(30) Foreign Application Priority Data

May 8, 2002   (GB) ................. 0210512.0
Nov. 21, 2002 (GB) ................. 0227262.3

(51) Int. Cl.
*A61K 31/17*   (2006.01)
*C07C 275/30*  (2006.01)
*C07C 275/32*  (2006.01)

(52) U.S. Cl. ....................... 514/598; 564/52

(58) Field of Classification Search ................. 514/521, 514/563, 596, 598; 558/410; 564/47, 52
See application file for complete search history.

(56) References Cited

U.S. PATENT DOCUMENTS

| 6,333,337 B1 * | 12/2001 | Gross et al. ................. 514/307 |
| 7,381,840 B2 * | 6/2008 | Tajimi et al. ................. 564/32 |
| 2008/0045546 A1 * | 2/2008 | Bouchon et al. ......... 514/258.1 |
| 2008/0058377 A1 * | 3/2008 | Mogi et al. ................. 514/319 |
| 2008/0275047 A1 * | 11/2008 | Tajimi et al. ............. 514/239.2 |

FOREIGN PATENT DOCUMENTS

| WO | 0050387 | 8/2000 |
| WO | WO 00/75106 | 12/2000 |
| WO | WO 2005/002551 A2 * | 1/2005 |

OTHER PUBLICATIONS

Office Action dated Apr. 19, 2007 in connection with U.S. Appl. No. 10/537,217.
Office Action dated Nov. 30, 2007 in connection with U.S. Appl. No. 10/537,217.
Office Action dated Jul. 2, 2008 in connection with U.S. Appl. No. 10/537,217.
Office Action dated Oct. 16, 2008 in connection with U.S. Appl. No. 10/574,122.

* cited by examiner

*Primary Examiner*—Kamal A Saeed
*Assistant Examiner*—Kristin Bianchi
(74) *Attorney, Agent, or Firm*—Baker Botts L.L.P.

(57) ABSTRACT

This invention relates to tetrahydro-naphthalene derivatives and salts thereof which is useful as an active ingredient of pharmaceutical preparations. The tetrahydro-naphthalene derivatives of the present invention have an excellent activity as VR1 antagonist and useful for the prophylaxis and treatment of diseases associated with VR1 activity, in particular for the treatment of urge urinary incontinence, overactive bladder, chronic pain, neuropathic pain, postoperative pain, rheumatoid arthritic pain, neuralgia, neuropathies, algesia, nerve injury, ischaemia, neurodegeneration, stroke, incontinence, inflammatory disorders such as asthma and COPD.

19 Claims, No Drawings

HYDROXY TETRAHYDRO-NAPHTHALENYLUREA DERIVATIVES

TECHNICAL FIELD

The present invention relates to hydroxy-tetrahydro-naphthalenylurea derivatives which are useful as an active ingredient of pharmaceutical preparations. The hydroxy-tetrahydro-naphthalenylurea derivatives of the present invention has vanilloid receptor (VR) antagonistic activity, and can be used for the prophylaxis and treatment of diseases associated with VR1 activity, in particular for the treatment of urge urinary incontinence, overactive bladder, chronic pain, neuropathic pain, postoperative pain, rheumatoid arthritic pain, neuralgia, neuropathies, algesia, nerve injury, ischaemia, neurodegeneration, stroke, incontinence and/or inflammatory disorders such as asthma and chronic obstructive pulmonary disease (COPD).

Urinary incontinence (UI) is the involuntary loss of urine. Urge urinary incontinence (UUI) is one of the most common types of UI together with stress urinary incontinence (SUI) which is usually caused by a defect in the urethral closure mechanism. UUI is often associated with neurological disorders or diseases causing neuronal damages such as dementia, Parkinson's disease, multiple sclerosis, stroke and diabetes, although it also occurs in individuals with no such disorders. One of the usual causes of UUI is overactive bladder (OAB) which is a medical condition referring to the symptoms of frequency and urgency derived from abnormal contractions and instability of the detrusor muscle.

There are several medications for urinary incontinence on the market today mainly to help treating UUI. Therapy for OAB is focused on drugs that affect peripheral neural control mechanisms or those that act directly on bladder detrusor smooth muscle contraction, with a major emphasis on development of anticholinergic agents. These agents can inhibit the parasympathetic nerves which control bladder voiding or can exert a direct spasmolytic effect on the detrusor muscle of the bladder. This results in a decrease in intravesicular pressure, an increase in capacity and a reduction in the frequency of bladder contraction. Orally active anticholinergic drugs such as propantheline (ProBanthine), tolterodine tartrate (Detrol) and oxybutynin (Ditropan) are the most commonly prescribed drugs. However, their most serious drawbacks are unacceptable side effects such as dry mouth, abnormal visions, constipation, and central nervous system-disturbances. These side effects lead to poor compliance. Dry mouth symptoms alone are responsible for a 70% non-compliance rate with oxybutynin. The inadequacies of present therapies highlight the need for novel, efficacious, safe, orally available drugs that have fewer side effects.

BACKGROUND ART

Vanilloid compounds are characterized by the presence of a vanillyl group or a functionally equivalent group. Examples of several vanilloid compounds or vanilloid receptor modulators are vanillin (4-hydroxy-3-methoxy-benzaldehyde), guaniacol (2-methoxy-phenol), zingerone (4-/4-hydroxy-3-methoxyphenyl/-2-butanon), eugenol-(2-methoxy4-/2-propenyl/phenol), and capsaicin (8-methy-N-vanillyl-6-noneneamide).

Among others, capsaicin, the main pungent ingredient in "hot" chili peppers, is a specific neurotoxin that desensitizes C-fiber afferent neurons. Capsaicin interacts with vanilloid receptors (VR1), which are predominantly expressed in cell bodies of dorsal root ganglia (DRG) or nerve endings of afferent sensory fibers including C-fiber nerve endings [Tominaga M, Caterina M J, Malmberg A B, Rosen T A, Gilbert H, Skinner K, Raumann B E, Basbaum A I, Julius D: The cloned capsaicin receptor integrates multiple pain-producing stimuli. Neuron. 21: 531-543, 1998]. The VR1 receptor was recently cloned [Caterina M J, Schumacher M A, Tominaga M, Rosen T A, Levine J D, Julius D: Nature 389: 816-824, (1997)] and identified as a nonselective cation channel with six transmembrane domains that is structurally related to the TRP (transient receptor potential) channel family. Binding of capsaicin to VR1 allows sodium, calcium and possibly potassium ions to flow down their concentration gradients, causing initial depolarization and release of neurotransmitters from the nerve terminals. VR1 can therefore be viewed as a molecular integrator of chemical and physical stimuli that elicit neuronal signals in a pathological conditions or diseases.

There are abundant of direct or indirect evidence that shows the relation between VR1 activity and diseases such as pain, ischaemia, and inflammatory (e.g., WO 99/00115 and 00/50387). Further, it has been demonstrated that VR1 transduce reflex signals that are involved in the overactive bladder of patients who have damaged or abnormal spinal reflex pathways [De Groat W C: A neurologic basis for: the overactive bladder. Urology 50 (6A Suppl): 36-52, 1997]. Desensitisation of the afferent nerves by depleting neurotransmitters using VR1 agonists such as capsaicin has been shown to give promising results in the treatment of bladder dysfunction associated with spinal cord injury and multiple sclerosis [(Maggi C A: Therapeutic potential of capsaicin-like molecules—Studies in animals and humans. Life Sciences 51: 1777-1781, 1992) and (DeRidder D; Chandiramani V;. Dasgupta P; VanPoppel H; Baert L; Fowler C J: Intravesical capsaicin as a treatment for refractory detrusor hyperreflexia: A dual center study with long-term followup. J. Urol. 158: 2087-2092, 1997)].

It is anticipated that antagonism of the VR1 receptor would lead to the blockage of neurotransmitter release, resulting in prophylaxis and treatment of the condition and diseases associated with VR1 activity.

It is therefore expected that antagonists of the VR1 receptor can be used for the prophylaxis and treatment of the condition and diseases including chronic pain, neuropathic pain, postoperative pain, rheumatoid arthritic pain, neuralgia, neuropathies, algesia, nerve injury, ischaemia, neurodegeneration, stroke, incontinence, inflammatory disorders such as asthma and COPD, urinary incontinence (UI) such as urge urinary incontinence (UUI), and/or overactive bladder.

WO 00/50387 discloses the compounds having a vanilloid agonist activity represented by the general formula:

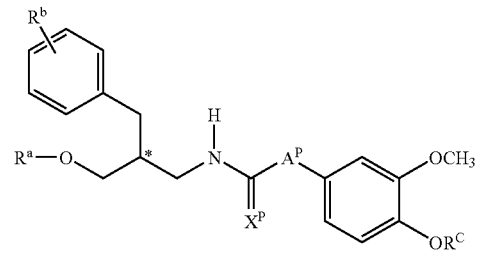

wherein;

$X^P$ is an oxygen or sulfur atom;

$A^P$ is —NHCH$_2$— or —CH$_2$—;

$R^a$ is a substituted or unsubstituted $C_{1-4}$ alkyl group, or $R^{a1}CO$—;

wherein $R^{a1}$ is an alkyl group having 1 to 18 carbon atoms, an alkenyl group having 2 to 18 carbon atoms, or substituted or unsubstituted aryl group having 6 to 10 carbon atoms;

$R^b$ is a hydrogen atom, an alkyl group having 1 to 6 carbon atoms, an alkoxy group having 1 to 6 carbon atoms, a haloalkyl group having 1 to 6 carbon atoms or a halogen atom;

$R^C$ is a hydrogen atom, an alkyl group having 1 to 4 carbon atom, an aminoalkyl, a diacid monoester or α-alkyl acid; and the asteric mark * indicates a chiral carbon atom, and their pharmaceutically acceptable salts.

WO 2000/61581 discloses amine derivatives represented by the general formula:

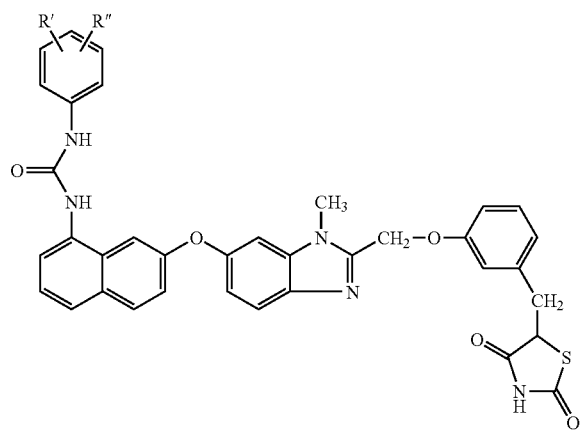

wherein (R', R") represent (F, F), (CF$_3$, H), or (iPr, iPr)

as useful agents for diabetes, hyperlipemia, arteriosclerosis and cancer.

WO 00/75106 discloses the compounds represented by the general formula:

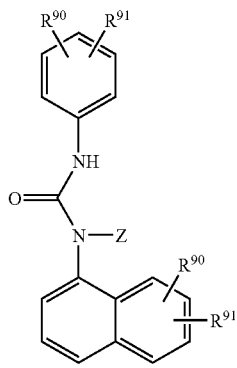

wherein

Z represents

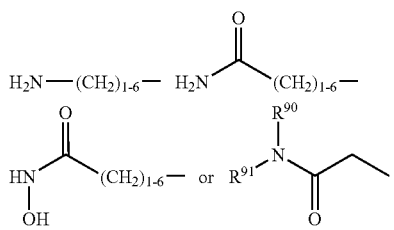

in which $R^{90}$ is hydrogen, $C_{1-12}$ alkyl, $C_{3-8}$ cycloalkyl, or the like: and $R^{91}$ is amino-$C_{1-6}$ alkyl, aminocarbonyl-$C_{1-6}$ alkyl, or hydroxyamino-carbonyl $C_{1-6}$ alkyl; and $R^{90}$ and $R^{91}$ are independently selected from the group consisting of H, $C_{1-6}$ alkyl, $C_{1-6}$ alkylthio, $C_{1-6}$ alkoxy, fluoro, chloro, bromo, iodo, and nitro;

as useful agents for treating MMP-mediated diseases in mammals.

WO 00/55152 discloses the compounds represented by the general formula:

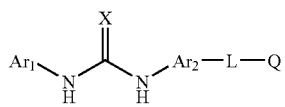

wherein

Ar$_1$ is heterocycle;

Ar$_2$ is tetrahydronapthy; and

L and Q are defined in this specification;

as useful agents for treating inflammation, immune relate disease, pain and diabetes.

However, none of these reference discloses simple hydroxy-tetrahydro-naphthalenylurea derivatives having VR1 antagonistic activity.

The development of a compound which has effective VR1 antagonistic activity and can be used for the prophylaxis and treatment of diseases associated with VR1 activity, in particular for the treatment of urinary incontinence, urge urinary incontinence, overactive bladder as well as pain, and/or inflammatory diseases such as asthma and COPD has been desired.

SUMMARY OF THE INVENTION

This invention is to provide a hydroxy-tetrahydro-naphthalenylurea derivative of the formula (I), their tautomeric and stereoisomeric form, and salts thereof:

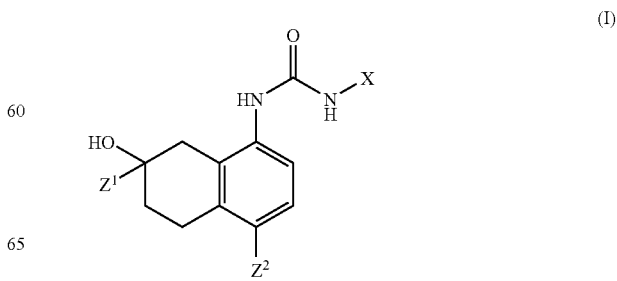

-continued wherein

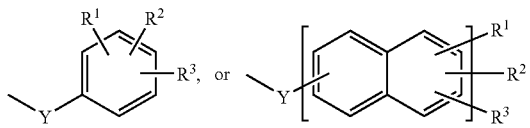

in which
Y represents a direct bond,

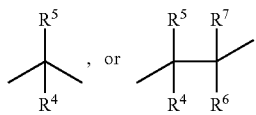

R$^1$, R$^2$ and R$^3$ independently represent hydrogen, halogen, hydroxy, nitro, carboxy, amino, C$_{1-6}$ alkylamino, di(C$_{1-6}$ alkyl) amino, C$_{3-8}$ cycloalkylamino, C$_{1-6}$ alkoxycarbonyl, phenyl, benzyl sulfonamide, C$_{1-6}$ alkanoyl, C$_{1-6}$ alkanoylamino, carbamoyl, C$_{1-6}$ alkylcarbamoyl, cyano, C$_{1-6}$ alkyl optionally substituted by cyano, C$_{1-6}$ alkoxycarbonyl or mono-, di-, or tri-halogen, C$_{1-6}$ alkoxy optionally substituted by mono-, di-, or tri-halogen, phenoxy optionally substituted by halogen or C$_{1-6}$ alkyl, or C$_{1-6}$ alkylthio optionally substituted by mono-, di-, or tri-halogen;

R$^4$, R$^5$, R$^6$ and R$^7$ independently represent hydrogen, C$_{1-6}$ alkyl or phenyl;

Z$^1$ represents hydrogen or C$_{1-6}$ alkyl; and

Z$^2$ represents hydrogen, halogen or C$_{1-6}$ alkyl.

The hydroxy-tetrahydro-naphthalenylurea derivatives of formula (I), their tautomeric and stereoisomeric form, and salts thereof surprisingly show excellent VR1 antagonistic activity. They are, therefore suitable especially for the prophylaxis and treatment of diseases associated with VR1 activity, in particular for the treatment of urge urinary incontinence and/or overactive bladder.

Preferably, the hydroxy-tetrahydro-naphthalenylurea derivatives of formula (I) are those wherein
X represents

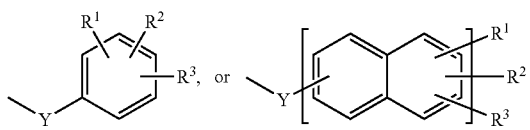

in which
Y represents a direct bond, or

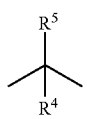

R$^1$, R$^2$ and R$^3$ independently represent hydrogen, halogen, hydroxy, nitro, carboxyl, amino, C$_{1-6}$ alkylamino, di(C$_{1-6}$ alkyl)amino, C$_{3-8}$ cycloalkylamino, C$_{1-6}$ alkoxycarbonyl phenyl, benzyl, sulfonamide, C$_{1-6}$ alkanoyl, C$_{1-6}$ alkanoylamino, carbamoyl, C$_{1-6}$ alkylcarbamoyl, cyano, C$_{1-6}$ alkyl optionally substituted by cyano, C$_{1-6}$ alkoxycarbonyl or mono-, di-, or tri-halogen, C$_{1-6}$ alkoxy optionally substituted by mono-, di-, or tri-halogen, phenoxy optionally substituted by halogen or C$_{1-6}$ alkyl, or C$_{1-6}$ alkylthio optionally substituted by mono-, di-, or tri-halogen;

R$^4$ and R$^5$ independently represent hydrogen or C$_{1-6}$ alkyl; and

Z$^1$ and Z$^2$ each represent hydrogen.

In another embodiment, the hydroxy-tetrahydro-naphthalenylurea derivatives of formula (I) can be those wherein
X represents

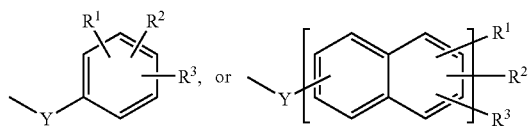

in which
Y represents a direct bond or

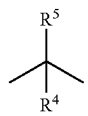

R$^1$, R$^2$ and R$^3$ independently represent hydrogen, halogen, di(C$_{1-6}$ alkyl)amino, C$_{3-8}$ cycloalkylamino, C$_{1-6}$ alkoxycarbonyl, C$_{1-6}$ alkyl optionally substituted by cyano, C$_{1-6}$ alkoxycarbonyl or mono-, di-, or tri-halogen, C$_{1-6}$ alkoxy optionally substituted by mono-, di-, or tri-halogen, phenoxy optionally substituted by halogen or C$_4$ alkyl, or C$_{1-6}$ alkylthio optionally substituted by mono-, di-, or tri-halogen;

R$^4$ and R$^5$ each represent hydrogen; and

Z$^1$ and Z$^2$ each represent hydrogen.

In another embodiment, the hydroxy-tetrahydro-naphthalenylurea derivatives of formula (I) can be those wherein
X represents

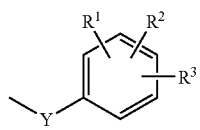

in which
Y represents a direct bond or

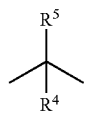

in which
R$^1$ and R$^2$ independently represent hydrogen, chloro, bromo, fluoro, cyclopentylamino, trifluoromethyl, or trifluoromethoxy;

R$^3$, R$^4$ and R$^5$ each represent hydrogen; and

Z$^1$ and Z$^2$ each represent hydrogen.

In another embodiment, the hydroxy-tetrahydro-naphthalenylurea derivatives of formula (I) can be those wherein
X represents

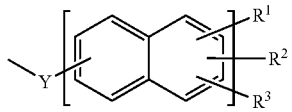

in which
Y represents direct bond or

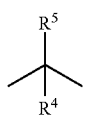

in which
$R^1$ and $R^2$ independently represent hydrogen, chloro, bromo, fluoro, cyclopentylamino, trifluoromethyl, or trifluoromethoxy;
$R^3$, $R^4$ and $R^5$ each represent hydrogen; and
$Z^1$ and $Z^2$ each represent hydrogen.

More preferably, said hydroxy-tetrahydro-naphthalenylurea derivative of the formula (I) is selected from the group consisting of:
N-[4-chloro-3-(trifluoromethyl)phenyl]-N'-(7-hydroxy-5,6,7,8-tetrahydro-1-naphthalenyl)urea;
N-(3-chlorophenyl)-N'-(7-hydroxy-5,6,7,8-tetrahydro-1-naphthalenyl)urea;
N-(7-hydroxy-5,6,7,8-tetrahydro-1-naphthalenyl)-N'-[3-(trifluoromethyl)phenyl]urea;
N-(7-hydroxy-5,6,7,8-tetrahydro-1-naphthalenyl)-N'-[4-(trifluoromethyl)phenyl]urea,
Ethyl 3-({[(7-hydroxy-5,6,7,8-tetrahydro-1-naphthalenyl)amino]carbonyl}amino)benzoate;
N-(7-hydroxy-5,6,7,8-tetrahydro-1-naphthalenyl)-N'-(1-naphthyl)urea;
N-(7-hydroxy-5,6,7,8-tetrahydro-1-naphthalenyl)-N'-(2-naphthyl)urea;
N-(3,4-dichlorophenyl)-N'-(7-hydroxy-5,6,7,8-tetrahydro-1-naphthalenyl)urea;
N-(7-hydroxy-5,6,7,8-tetrahydro-1-naphthalenyl)-N'-(4-isopropylphenyl)urea,
N-(7-hydroxy-5,6,7,8-tetrahydro-1-naphthalenyl)-N'-(4phenoxyphenyl)urea
N-[4-chloro-3-(trifluoromethyl)phenyl]-N'-[(7-hydroxy-5,6,7,8-tetrahydro-1-naphthalenyl]urea;
N-[4-chloro-3-(trifluoromethyl)phenyl]-N'-[(7S)-7-hydroxy-5,6,7,8-tetrahydro-1-naphthalenyl]urea;
N-[4-chloro-3-(trifluoromethyl)phenyl]-N'-[(7R)-7-hydroxy-5,6,7,8-tetrahydro-1-naphthalenyl]urea;
N-(7-hydroxy-5,6,7,8-tetrahydro-1-naphthalenyl)-N'-phenylurea;
N-(4-chlorophenyl)-N'-(7-hydroxy-5,6,7,8-tetrahydro-1-naphthalenyl)urea;
N-(7-hydroxy-5,6,7,8-tetrahydro-1-naphthalenyl)N'-[2-(trifluoromethyl)phenyl]urea;
N-(7-hydroxy-5,6,7,8-tetrahydro-1-naphthalenyl)N'-[4-(trifluoromethyl)phenyl]urea;
N-(3,4dichlorophenyl)-N'-(7-hydroxy-5,6,7,8-tetrahydro-1-naphthalenyl)urea;
N-(7-hydroxy-5,6,7,8-tetrahydro-1-naphthalenyl)-N'-[4-(trifluoromethoxy)phenyl]urea;
N-(7-hydroxy-5,6,7,8-tetrahydro-1-naphthalenyl)N'-[4-(trifluoromethoxy)benzyl]urea;
N-(7-hydroxy-5,6,7,8-tetrahydro-1-naphthalenyl)N'-(2,4,6-trimethoxybenzyl)urea;
N-(2,6-difluorobenzyl)-N'-(7-hydroxy-5,6,7,8-tetrahydro-1-naphthalenyl)urea;
N-[(7R)-7-hydroxy-5,6,7,8-tetrahydro-1-naphthalenyl]-N'-[4-(trifluoromethyl)benzyl]urea;
N-[(7S)-7-hydroxy-5,6,7,8-tetrahydro-1-naphthalenyl]-N'-[4-(trifluoromethyl)-benzyl]urea;
N-[(7R)-7-hydroxy-5,6,7,8-tetrahydro-1-naphthalenyl]-N'-[4-(trifluoromethoxy)-benzyl]urea;
N-[(7S)-7-hydroxy-5,6,7,8-tetrahydro-1-naphthalenyl]-N'-[4-(trifluoromethoxy)-benzyl]urea;
N-[2-(4-chlorophenyl)ethyl]-N'-(7-hydroxy-5,6,7,8-tetrahydro-1-naphthalenyl)urea; and
N-[3-fluoro-4-(trifluoromethyl)benzyl]-N'-(7-hydroxy-5,6,7,8-tetrahydro-1-naphthalenyl)urea.

In the context of the present invention, the substituents, if not stated otherwise, in general have the following meaning:
The Alkyl per se and "alk" and "alkyl" in alkoxy, alkanoyl, alkylamino, alkylaminocarbonyl, alkylaminosulphonyl, alkylsulphonylamino, aloxycarbonyl, alkoxycarbonylamino and alkanoylamino represent a linear or branched alkyl radical having generally 1 to 6, preferably 1 to 4 and particularly preferably 1 to 3 carbon atoms, representing illustratively and preferably methyl, ethyl, n-propyl, isopropyl, tert-butyl, n-pentyl and n-hexyl.

Alkoxy illustratively and preferably represents methoxy, ethoxy, n-propoxy, iso-propoxy, tert-butoxy, n-pentoxy and n-hexoxy.

Alkanoyl illustratively and preferably represents acetyl and propanoyl.

Alkylamino represents an alkylamino radical having one or two (independently selected) alkyl substituents, illustratively and preferably representing methylamino, ethylamino, n-propylamino, isopropylamino, tert-butylamino, n-pentylamino, n-hexyl-amino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Alkylaminocarbonyl or alkylcarbamoyl represents an alkylaminocarbonyl radical having one or two (independently selected) alkyl substituents, illustratively and preferably representing methylaminocarbonyl, ethylaminocarbonyl, n-propylamino-carbonyl, isopropylamino-carbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-t-butyl-N-methylaminocarbonyl, N-ethyl-N-n-pentylamino-carbonyl and N-n-hexyl-N-methylaminocarbonyl.

Alkoxycarbonyl illustratively and preferably represents-methoxycarbonyl, ethoxycarbonyl, n-propoxycarbonyl, isopropoxycarbonyl, tert-butoxycarbonyl, n-pentoxycarbonyl and -n-hexoxycarbonyl. Alkoxycarbonylamino illustratively and preferably represents methoxycarbonylamino, ethoxycarbonylamino, n-propoxycarbonylamino, isopropoxycarbonylamino, tert-butoxycarbonylamino, n-pentoxycarbonylamino and n-hexoxycarbonylamino.

Alkanoylamino illustratively and preferably represents acetylamino and ethylcarbonylamino.

Cycloalkyl per se and in cycloalkylamino and in cycloalkylcarbonyl represents a cycloalkyl group having generally 3 to 8 and preferably 5 to 7 carbon atoms, illustratively and preferably representing cyclopropyl, cyclobutyl, cyclopentyl cyclohexyl and cycloheptyl.

Cycloalkylamino represents a cycloalkylamino radical having one or two (independently selected) cycloalkyl substituents, illustratively and preferably representing cyclopropylamino, cyclobutylamino, cyclopentylamino, cyclohexylamino and cycloheptylamino.

Halogen represents fluorine, chlorine, bromine and iodine.

Preferably, the medicament of the present invention further comprise one or more pharmaceutically acceptable carriers and/or excipients.

The hydroxy-tetrahydro-naphthalenylurea derivatives of the formula (I), their tautomeric and stereoisomeric form, and salts thereof are effective for treating or preventing a disease selected from the group consisting of urge urinary incontinence, overactive bladder, chronic pain, neuropathic pain, postoperative pain, rheumatoid arthritic pain, neuralgia, neuropathies, algesia, nerve injury, ischaemia, neuro-degeneration and/or stroke, as well as inflammatory diseases such as asthma and COPD since the diseases also relate to VR1 activity.

The compounds are additionally of use for the treatment and prophylaxis of Neuropathic pain, is a form of pain often associated with herpes zoster and post-herpetic neuralgia, painful diabetic neuropathy, neuropathic low back pain, posttraumatic and postoperative neuralgia, neuralgia due to nerve compression and other neuralgias, phantom pain, complex regional pain syndromes, infectious or parainfectious neuropathies like those associated with HIV infection, pain associated with central nervous system disorders like multiple sclerosis or Parkinson disease or spinal cord injury or traumatic brain injury, and post-stroke pain.

Furthermore, the compounds are useful for the treatment of musculoskeletal pain, a form of pain often associated with osteoarthritis or rheumatoid arthritis or other forms of arthritis, and back pain.

In addition, the compounds are useful for the treatment of pain associated with cancer, including visceral or neuropathic pain associated with cancer or cancer treatment.

The compounds are furthermore useful for the treatment of visceral pain e.g. pain associated with obstruction of hollow viscus like gallstone colik, pain associated with irritable bowel syndrome, pelvic pain, vulvodynia, orchialgia or prostatodynia.

The compounds are also useful for the treatment of pain associated with inflammatory lesions of joints, skin, muscles or nerves.

The compounds are of use for the treatment of orofascial pain and headache, e.g. migraine or tension-type headache.

EMBODIMENT OF THE INVENTION

The compound of the formula (I) of the present invention can be, but not limited to be, prepared by the methods [A],[B], [C], [D], [E], [F], or [G] below. In some embodiments, one or more of the substituents, such as amino group, carboxyl group, and hydroxyl group of the compounds used as starting materials or intermediates are advantageously protected by a protecting group known to those skilled in the art. Examples of the protecting groups are described in "Protective Groups in Organic Synthesis (3rd Edition)" by Greene and Wuts, John Wiley and Sons, New York 1999.

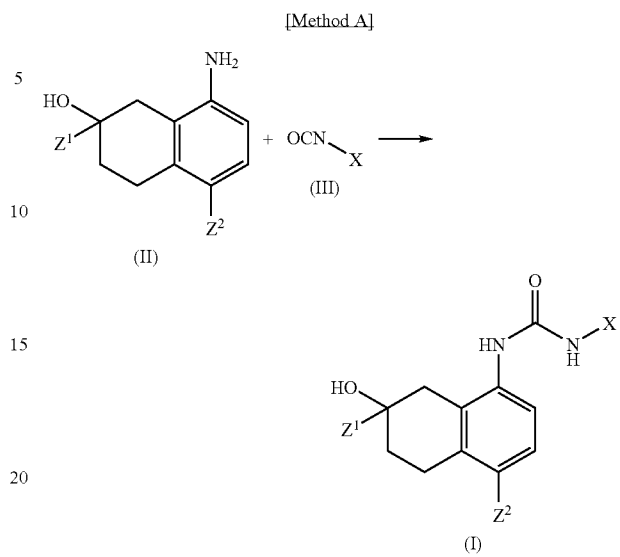

The compound of the formula (I) (wherein X, $Z^1$ and $Z^2$ are the same as defined above) can be prepared by the reaction of the compound of the formula (II) (wherein $Z^1$ and $Z^2$ are the same as defined above) and isocyanate (III) (wherein X is the same as defined above).

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction can be carried out in the presence of organic base such as pyridine or triethylamine.

The reaction temperature can be optionally set depending on the compounds to be reacted. The reaction temperature is usually, but not limited to, about room temperature to 100° C. The reaction may be conducted for, usually, 30 minutes to 48 hours and preferably 1 to 24 hours.

The compound of the formula (II) and isocyanate (III) are commercially available or can be prepared by the use of known techniques.

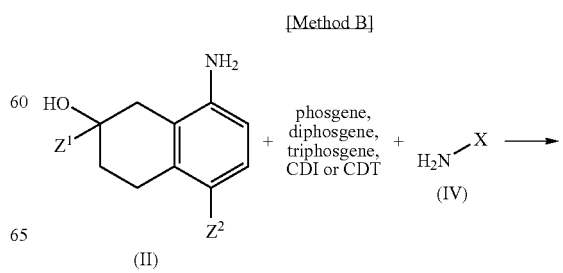

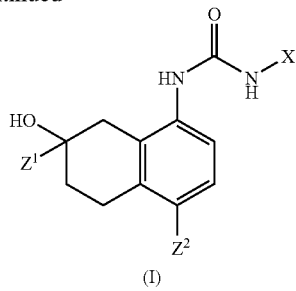

The compound of the formula (I) (wherein X, $Z^1$ and $Z^2$ are the same as defined above) can be prepared by reacting the compound of the formula (II) (wherein $Z^1$ and $Z^2$ are the same as defined above) with phosgene, diphosgene, triphosgene, 1,1-carbonyldiimidazole (CDT), or 1,1'-carbonyldi(1,2,4-triazole)(CDT), and then adding the compound of the formula (IV) (wherein X is the same as defined above) to the reaction mixture.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); and others. Optionally, two or more of the solvents selected from the listed above can be mixed and used.

The reaction temperature can be optionally set depending on the compounds to be reacted. The reaction temperature is usually, but not limited to, about 20° C. to 50° C. The reaction may be conducted for, usually, 30 minutes to 10 hours and preferably 1 to 24 hours.

Phosgene, diphosgene, triphosgene, CDI, and CDT are commercially available and the compound of the formula (IV) is commercially available or can be prepared by the use of known techniques.

[Method C]

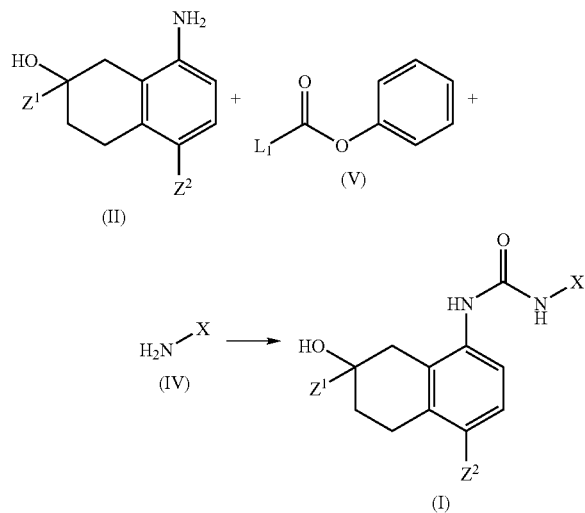

The compound of the formula (D (wherein X, $Z^1$ and $Z^2$ are the same as defined above) can be prepared by reacting the compound of the formula (II) (wherein $Z^1$ and $Z^2$ are the same as defined above) and the compound of the formula (V) (wherein $L_1$ represents halogen atom such as chlorine, bromine, or iodine atom) and then adding the compound of the formula (IV) (wherein X is the same as defined above) to the reaction mixture.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); and others. Optionally, two or more of the solvents selected from the listed above can be mixed and used.

The reaction temperature can be optionally set depending on the compounds to be reacted. The reaction temperature is usually, but not limited to, about 30° C. to 120° C.

The reaction may be conducted for, usually, 1 hour to 48 hours and preferably 2 to 24 hours.

The reaction can be advantageously carried out in the presence of a base including, for instance, organic amines such as pyridine, triethylamine and N,N-diisopropylethylamine, dimethylaniline, diethylaniline, 4-dimethylaminopyridine, and others.

The compound (V) is commercially available or can be prepared by the use of known techniques.

[Method D]

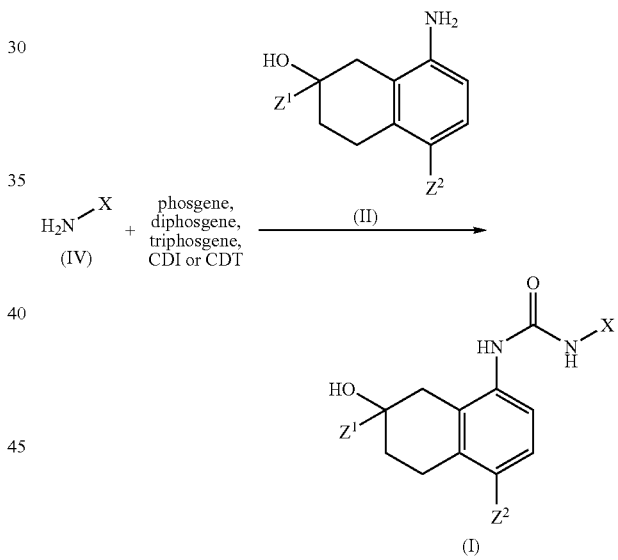

The compound of the formula (I) (wherein X, $Z^1$ and $Z^2$ are the same as defined above) can be prepared by reacting the compound of the formula (IV) (wherein X is the same as defined above) with phosgene, diphosgene, triphosgene, 1,1-carbonyl-diimidazole (CDI), or 1,1'-carbonyldi(1,2,4-triazole)(CDT), and then adding the compound of the formula (II) (wherein $Z^1$ and $Z^2$ are the same as defined above) to the reaction mixture.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethyoxyethane; aromatic hydrocarbons such as benzene, toluene and xylene; nitrites such as acetonitrile; amides such as N,N dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others.

Optionally, two or more of the solvents selected from the listed above can be mixed and used.

The reaction temperature can be optionally set depending on the compounds to be reacted. The reaction temperature is usually, but not limited to, about 30° C. to 100° C.

The reaction may be conducted for, usually, 30 minutes to 40 hours and preferably 1 to 24 hours.

[Method E]

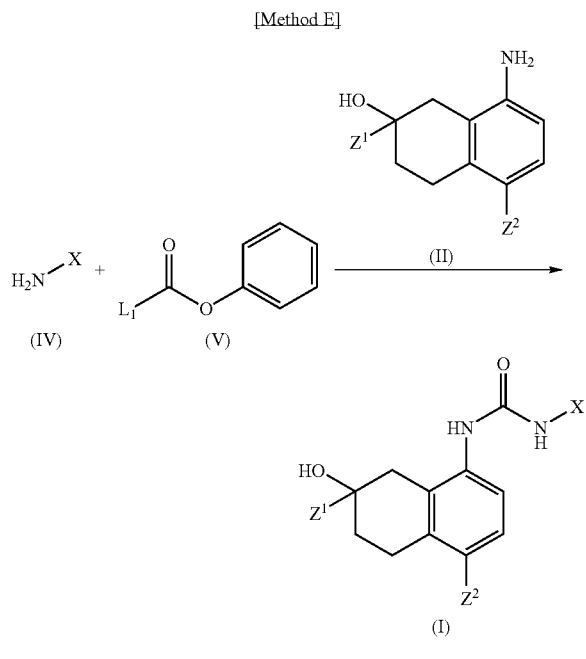

The compound of the formula (I) (wherein X, $Z^1$ and $Z^2$ are the same as defined above) can be prepared by reacting the compound of the formula (IV) (wherein X is the same as defined above) and the compound of the formula (V) (wherein $L_1$ represents halogen atom such as chlorine, bromine, or iodine atom) and then adding the compound of the formula (II) (wherein $Z^1$ and $Z^2$ are the same as defined above) to the reaction mixture.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitrites such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); and others. Optionally, two or more of the solvents selected from the listed above can be mixed and used.

The reaction temperature can be optionally set depending on the compounds to be reacted. The reaction temperature is usually, but not limited to, about 30° C. to 120° C.

The reaction may be conducted for, usually, 1 hour to 48 hours and preferably 2 to 24 hours.

The reaction can be advantageously carried out in the presence of a base including, for instance, organic amines such as pyridine, triethylamine and N,N-diisopropylethylamine, dimethylaniline, diethylaniline, 4-dimethylaminopyridine, and others.

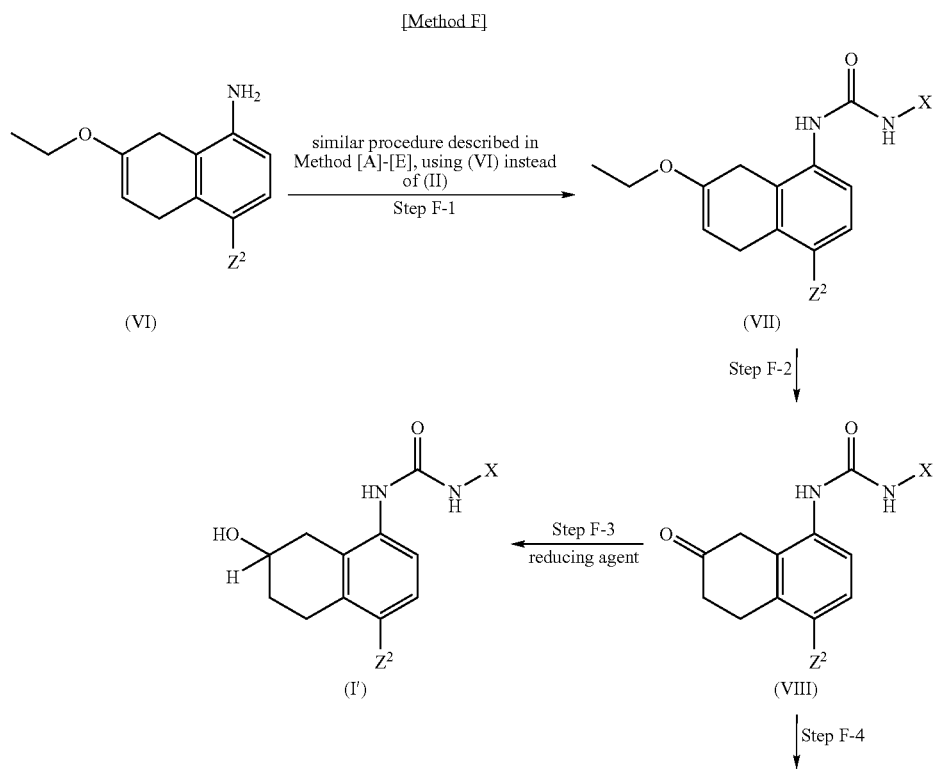

-continued

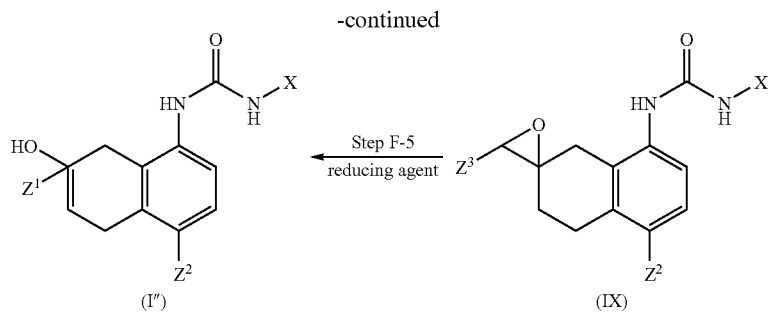

The compound of the formula (I') (wherein X and $Z^2$ are the same as defined above) can be prepared by the following procedures;

In the Step F-1, the compound of the formula (VII) (wherein X and $Z^2$ are the same as defined above) can be prepared in the similar manner as described in Method [A], [B], [C], [D], or [E] for the preparation of the compound of the formula (I) by using a compound of the formula (VI) (wherein $Z^2$ is the same as defined above) instead of the compound of the formula (II).

In the Step F-2, the compound of the formula (VIII) (wherein X and $Z^2$ are the same as defined above) can be prepared by reacting the compound of the formula (VI) wherein X and $Z^2$ are the same as defined above) with an acid such as hydrochloric acid.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; alcohols such as methanol, ethanol; water and others. Optionally, two or more of the solvents selected from the listed above can be mixed and used.

The reaction temperature can be optionally set depending on the compounds to be reacted. The reaction temperature is usually, but not limited to, about 20° C. to 100° C. The reaction may be conducted for, usually, 30 minutes to 10 hours and preferably 1 to 24 hours.

In the Step F-3, the compound of the formula (I') (wherein X and $Z^2$ are the same as defined above) can be prepared by reacting the compound of the formula (VIII) (wherein X and $Z^2$ are the same as defined above) with reducing agent such as sodium borohydride or lithium aluminum hydride.

The reaction may be carried out in a solvent including, for instance, ethers such as diethyl ether, isopropyl ether, dioxane and tetrahydrofuran (THF) and 1,2-di-methoxyethane; aliphatic hydrocarbons such as n-hexane, cyclohexane; aromatic hydrocarbons such as benzene, toluene and xylene; alcohols such as methanol, ethanol, isopropanol and others. Optionally, two or more of the solvents selected from the listed above can be mixed and used.

The reaction temperature can be optionally set depending on the compounds to be reacted. The reaction temperature is usually, but not limited to, about –20° C. to 50° C.

The reaction may be conducted for, usually, 30 minutes to 10 hours and preferably 1 to 24 hours.

The compound of the formula (I'') (wherein X and $Z^2$ are the same as defined above and $Z^1$ is $C_{1-6}$ alkyl) can be prepared by the following procedures in two steps.

In the Step F-4, the compound of the formula (IX) (wherein X and $Z^2$ are the same as defined above and $Z^3$ is hydrogen or $C_{1-5}$ alkyl) can be prepared by reacting the compound of the formula (VIII) (wherein X and $Z^2$ are the same as defined above) with tri($C_{1-6}$ alkyl)oxosulfonium salt such as trimethyloxosulfonium iodide.

The reaction may be carried out in a solvent including, for instance, ethers such as diethyl ether, isopropyl ether, dioxane and tetrahydrofuran (THF) and 1,2-dimethoxyethane; aliphatic hydrocarbons such as n-hexane, cyclohexane; aromatic hydrocarbons such as benzene, toluene and xylene; and others. Optionally, two or more of the solvents selected from the listed above can be mixed and used.

The reaction temperature can be optionally set depending on the compounds to be reacted. The reaction temperature is usually, but not limited to, about –20° C. to 50° C. The reaction may be conducted for, usually, 30 minutes to 10 hours and preferably 1 to 24 hours.

In the Step F-5, the compound of the formula (I'') (wherein X, $Z^2$ are the same as defined above and $Z^1$ is $C_{1-6}$ alkyl) can be prepared by reacting the compound of the formula (IX) (wherein X and $Z^2$ are the same as defined above and $Z^3$ is hydrogen or $C_{1-5}$ alkyl) with reducing agent such as sodium borohydride or lithium aluminum hydride.

The reaction may be carried out in a solvent including, for instance, ethers such as diethyl ether, isopropyl ether, dioxane -and tetrahydrofuran (THF) and 1,2-dimethoxyethane; aliphatic hydrocarbons such as n-hexane, cyclohexane; aromatic hydrocarbons such as benzene, toluene and xylene; and others. Optionally, two or more of the solvents selected from the listed above can be mixed and used.

The reaction temperature can be optionally set depending on the compounds to be reacted. The reaction temperature is usually, but not limited to, about 20° C. to 50° C.

The reaction may be conducted for, usually, 30 minutes to 10 hours and preferably 1 to 24 hours.

The compound (VI) is commercially available or can be prepared by the use of known techniques.

[Method G]

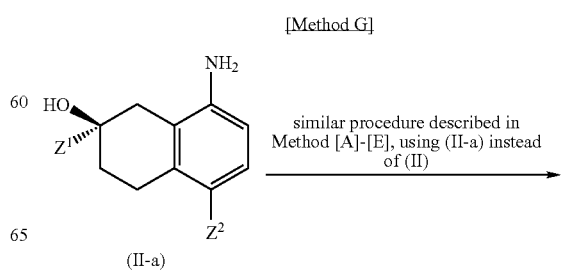

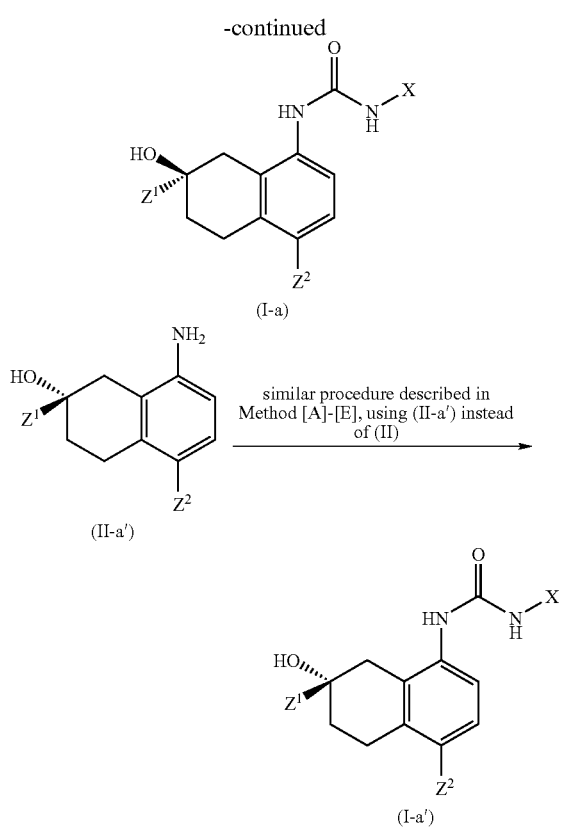

The stereoisomeric form of the compound (I), R form (I-a) R form (I-a) (Wherein X Z¹ and Z² are the same as defined above) can be prepared in the similar manner as described in Method [A], [B], [C], [D], or [E] for the preparation of the compound of the formula (I) by using a compound of the formula (II-a) (wherein Z¹ and Z² are the same as defined above) instead of the compound of the formula (II).

The stereoisomeric form of the compound (I), S form (I-a') (wherein X, Z¹ and Z² are the same as defined above) can be prepared in the similar manner as described in Method [A], [B], [C], [D], or [E] for the preparation of the compound of the formula (I) by using a compound of the formula (II-a') (wherein Z¹ and Z² are the same as defined above) instead of the compound of the formula (II).

The compound (II-a) or (II-a') can be prepared by the use of known techniques.

When the compound shown by the formula (I) or a salt thereof has an asymmetric carbon in the structure, their optically active compounds and racemic mixtures are also included in the scope of the present invention.

Typical salts of the compound shown by the formula (I) include salts prepared by reaction of the compounds of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydriodic acid and the like, and organic acids, such as, without limitation, p-toluene-sulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethylamine, tris (hydroxymethyl)aminomethane, and the like. Examples of inorganic bases include sodium hydroxide, potassium hydroxide, potassium carbonate, sodium carbonate, sodium bicarbonate, potassium bicarbonate, calcium hydroxide, calcium carbonate, and the like.

The compound of the present invention or a salt thereof, depending on its substituents, may be modified to form lower alkylesters or known other esters; and/or hydrates or other solvates. Those esters, hydrates, and solvates are included in the scope of the present invention.

The compound of the present invention may be administered in oral forms, such as, without limitation normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well-known to those of ordinary skill in the pharmaceutical arts. The compounds of the present invention can be administered in intranasal form via topical use of suitable intranasal vehicles, or via transdermal routes, using transdermal delivery systems well-known to those of ordinary skilled in the art.

The dosage regimen with the use of the compounds of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds of the present invention are preferably formulated prior to administration together with one or more pharmaceutically-acceptable excipients. Excipients are inert substances such as, without limitation carriers, diluents, flavoring agents, sweeteners, lubricants, solubilizers, suspending agents, binders, tablet disintegrating agents and encapsulating material.

Yet another embodiment of the present invention is pharmaceutical formulation comprising a compound of the invention and one or more pharmaceutically-acceptable excipients that, are compatible with the other ingredients of the formulation and not deleterious to the recipient thereof. Pharmaceutical formulations of the invention are prepared by combining a therapeutically effective amount of the compounds of the invention together with one or more pharmaceutically-acceptable excipients therefore. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely divided solid which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carriers, such as sterile water, sterile organic solvent, or a mixture of both sterile water and sterile organic solvent The active ingredient can also be dissolved in a suitable organic solvent, for example, aqueous propylene glycol. Other compositions can be made by dispersing the finely divided active ingredient in aqueous, starch or sodium carboxymethyl cellulose solution or in a suitable oil.

The formulation may be in unit dosage form, which is a physically discrete unit containing a unit dose, suitable for administration in human or other mammals. A unit dosage form can be a capsule or tablets, or a number of capsules or tablets. A "unit -dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the present invention, when used for the indicated effects, will range from about 0.01 mg/kg/day to about 100 mg/kg/day, preferably from 0.1 mg/kg/day to 30 mg/kg/day, and most preferably from about 0.5 mg/kg/day to about 10 mg/kg/day. In the case of parenteral administration, it has generally proven advantageous to administer quantities of about 0.001 to 100mg/kg/day, preferably from 0.01 mg/kg/day to 1 mg/kg/day. The compounds of the present invention may be administered in a single daily dose, or the total daily dose may be administered in divided doses, two, three, or more times per day. Where delivery is via transdermal forms, of course, administration is continuous.

EXAMPLES

The present invention will be described as a form of examples, but they should by no means be construed as defining the metes and bounds of the present invention.

In the examples below, all quantitative data, if not stated otherwise, relate to percentages by weight.

Mass spectra were obtained using electrospray (ES) ionization techniques (micromass Platform LC). Melting points are uncorrected. Liquid Chromatography-Mass spectroscopy (LC-MS) data were recorded on a Micromass Platform LC with Shimadzu Phenomenex ODS column(4.6 mmϕ×30 mm) flushing a mixture of acetonitrile-water (9:1 to 1:9) at 1 ml/min of the flow rate. TLC was performed on a precoated silica gel plate (Merck silica gel 60 F-254). Silica gel (WAKO-gel C-200 (75-150 μm)) was used for all column chromatography separations. All chemicals were reagent grade and were purchased from Sigma-Aldrich, Wako pure chemical industries, Ltd., Tokyo kasei kogyo co. Ltd., Arch corporation.

All starting materials are commercially available or can be prepared using methods cited in the literature.

The effect of the present compounds were examined by the following assays and pharmacological tests.

[Measurement of capsaicin-induced $Ca^{2+}$ influx in the human VR1-transfected CHO cell line] (Assay 1)

(1) Establishment of the Human VR1-CHOluc9aeq Cell Line

Human vanilloid receptor (hVR1) cDNA was cloned from libraries of axotomized dorsal root ganglia (WO 00/29577). The cloned hVR1 cDNA was constructed with pcDNA3 vector and transfected into a CHOluc9aeq cell line. The cell line contains aequorin and CRE-luciferase reporter genes as read-out signals. The transfectants were cloned by limiting dilution in selection medium (DMEM/F12 medium (Gibco BRL) supplemented with 10% FCS, 1.4 mM Sodium pyruvate, 20 mM HEPES, 0.15% Sodium bicarbonate, 100 U/ml penicillin, 100 μg/ml streptomycin, 2 mM glutamine, non-essential amino acids and 2 mg/ml G418). $Ca^{2+}$ influx was examined in the capsaicin-stimulated clones. A high responder clone was selected and used for further experiments in the project. The human VR1-CHOluc9aeq cells were maintained in the selection medium and passaged every 3-4 days at 1-2.5×10$^5$ cells/flask (75 mm$^2$).

(2) Measurement of $Ca^{2+}$ Influx Using FDSS-3000

Human VR1-CHOluc9aeq cells were suspended in a culture medium which is the same as the selection medium except for G418 and seeded at a density of 1,000 cells per well into 384-well plates (black walled clear-base/Nalge Nunc International). Following the culture for 48 hrs the medium was changed to 2 μM Fluo-3 AM (Molecular Probes) and 0.02% Puronic F-127 in assay buffer (Hank's balanced salt solution (HBSS), 17 mM HEPES (pH7.4), 1 mM Probenecid, 0.1% BSA) and the cells were incubated for 60 min at. 25° C. After washing twice with assay buffer the cells were incubated with a test compound or vehicle for 20 min at 25° C. Mobilization of cytoplasmic $Ca^{2+}$ was measured by FDSS-3000 ($\lambda_{ex}$=488 nm, $\lambda_{em}$=540 nm/Hamamatsu Photonics) for 60 sec after the stimulation with 10 nM capsaicin. Integral R was calculated and compared with controls.

[Measurement of the Capsaicin-Induced $Ca^{2+}$ Influx in Primary Cultured Rat Dorsal Root Ganglia Neurons] (Assay 2)

(1) Preparation of Rat Dorsal Root Ganglia Neurons

New born Wister rats (5-11 days) were sacrificed and dorsal root ganglia (DRG) was removed. DRG was incubated with 0.1% trypsin (Gibco BRL) in PBS(−) (Gibco BRL) for 30 min at 37° C., then a half volume of fetal calf serum (FCS) was added and the cells were spun down. The DRG neuron cells were resuspended in Ham F12/5% FCS/5% horse serum (Gibco BRL) and dispersed by repeated pipetting and passing through 70 μm mesh Falcon). The culture plate was incubated for 3 hours at 37° C. to remove contaminating Schwann cells. Non-adherent cells were recovered and further cultured in laminin-coated 384 well plates (Nunc) at 1×10$^4$ cells/

50 μl/well for 2 days in the presence of 50 ng/ml recombinant rat NGF (Sigma) and 50 μM 5-fluorodeoxyuridine (Sigma).

(2) $Ca^{2+}$ Mobilization Assay

DRG neuron cells were washed twice with HBSS supplemented with 17 mM HEPES (pH 7.4) and 0.1% BSA. After incubating with 2 μM fluo-3AM (Molecular Probe), 0.02% PF127 (Gibco BRL) and 1 mM probenecid (Sigma) for 40 min at 37° C., cells were washed 3 times. The cells were incubated with VR1 antagonists or vehicle (dimethylsulphoxide) and then with 1 μM capsaicin in FDSS-6000 ($\lambda_{ex}$=480 nm, $\lambda_{em}$=520 nm/Hamamatsu Photonics). The fluorescence changes at 480 nm were monitored for 2.5 min. Integral R was calculated and compared with controls.

[Organ Bath Assay to Measure the Capsaicin-Induced Bladder Contraction] (Assay 3)

Male Wistar rats (10 week old) were anesthetized with ether and sacrificed by dislocating the necks. The whole urinary bladder was excised and placed in oxygenated Modified Krebs-Henseleit solution (pH 7.4) of the following composition (112 mM NaCl, 5.9 mM KCl, 1.2 MM $MgCl_2$, 1.2 mM $NaH_2PO_4$, 2 mM $CaCl_2$, 2.5 mM $NaHCO_3$, 12 mM glucose). Contractile responses of the urinary bladder were studied as described previously [Maggi C A et al: Br. J. Pharmacol. 108: 801-805, 1993]. Isometric tension was recorded *under a load of 1 g using longitudinal strips of rat detrusor muscle. Bladder strips were equilibrated for 60 min before each stimulation. Contractile response to 80 mM KCl was determined at 15 min intervals until reproducible responses were obtained. The response to KCl was used as an internal standard to evaluate the maximal response to capsaicin. The effects of the compounds were investigated by incubating the strips with compounds for 30 min prior to the stimulation with 1 μM capsaicin (vehicle: 80% saline, 10% EtOH, and 10% Tween 80). One of the preparations made from the same animal was served as a control while the others were used for evaluating compounds. Ratio of each capsaicin-induced contraction to the internal standard (i.e. KCl-induced contraction) was calculated and the effects of the test compounds on the capsaicin-induced contraction were evaluated.

[Measurement of $Ca^{2+}$ Influx in the Human P2X1-Transfected CHO Cell Line]

(1) Preparation of the Human P2X1-Transfected CHOluc9aeq Cell Line

Human P2X1-transfected CHOluc9aeq cell line was established and maintained in Dulbecco's modified Eagle's medium (DMEM/F12) supplemented with 7.5% FCS, 20 mM HBEPES-KOH (pH 7.4), 1.4 mM sodium pyruvate, 100 U/ml penicillin, 100 μg/ml streptomycin, 2 mM glutamine (Gibco BRL) and 0.5 Units/ml apyrase (grade I, Sigma). The suspended cells were seeded in each well of 384well optical bottom black plates (Nalge Nunc International) at $3\times10^3$/50 μl/well. The cells were cultured for following 48 hrs to adhere to the plates.

(2) Measurement of the Intracellular $Ca^{2+}$ Levels

P2X1 receptor agonist-mediated increases in cytosolic $Ca^{2+}$ levels were measured using a fluorescent $Ca^{2+}$ chelating dye, Fluo-3 AM (Molecular Probes). The plate-attached cells were washed twice with washing buffer (HBSS, 17 mM HEPES-KOH (pH 7.4), 0.1% BSA and 0.5 units/ml apyrase), and incubated in 40 μl of loading buffer (1 μM Fluo-3 AM, 1 mM probenecid, 1 μM cyclosporin A, 0.01% pluronic (Molecular Probes) in washing buffer) for 1 hour in a dark place. The plates were washed twice with 40 μl washing buffer and 35 μl of washing buffer were added in each well with 5 μl of test compounds or 2',3'-o-(2,4,6-trinitrophenyl) adenosine 5'-triphpsphate (Molecular Probes) as a reference. After further incubation for 10 minutes in dark 200 nM α, β-methylene ATP agonist was added to initiate the $Ca^{2+}$ mobilization. Fluorescence intensity was measured by FDSS-6000 ($\lambda_{ex}$=410 nm, $\lambda_{em}$=510 nm/Hamamatsu Photonics) at 250 msec intervals. Integral ratios were calculated from the data and compared with that of a control.

[Measurement of Capsaicin-Induced Bladder Contraction in Anesthetized Rats] (Assay 4)

(1) Animals

Female Sprague-Dawley rats (200~250 g/Charles River Japan) were used.

(2) Catheter Implantation

Rats were anesthetized by intraperitoneal administration of urethane (Sigma) at 1.2 g/kg. The abdomen was opened through a midline incision, and a polyethylene catheter (BECTON DICKINSON, PE50) was implanted into the bladder through the dome. In parallel, the inguinal region was incised, and a polyethylene catheter (Hibiki, size 5) filled with 2 IU/ml of heparin (Novo Heparin, Aventis Pharma) in saline (Otsuka) was inserted into a common iliac artery.

(3) Cystometric Investigation

The bladder catheter was connected via T-tube to a pressure transducer (Viggo-Spectramed Pte Ltd, DT-XXAD) and a microinjection pump (TERUMO). Saline was infused at room temperature into the bladder at a rate of 2.4 ml/hr. Intravesical pressure was recorded continuously on a chart pen recorder (Yokogawa). At least three reproducible micturition cycles, corresponding to a 20-minute period, were recorded before a test compound administration and used as baseline values.

(4) Administration of Test Compounds and Stimulation of Bladder with Capsaicin

The saline infusion was stopped before administrating compounds. A testing compound dissolved in the mixture of ethanol, Tween 80 (ICN Biomedicals Inc.) and saline (1:1:8, v/v/v) was administered intraarterially at 10 mg/kg. 2 min after the administration of the compound 10 μg of capsaicin (Nacalai Tesque) dissolved in ethanol was administered intraarterially.

(5). Analysis of Cystometry Parameters

Relative increases in the capsaicin-induced intravesical pressure were analyzed from the cystometry data The capsaicin-induced bladder pressures were compared with the maximum bladder pressure during micturition without the capsaicin stimulation. The testing compounds-mediated inhibition of the increased bladder pressures was evaluated using Student's t-test. A probability level less than 5% was accepted as significant difference.

[Measurement of Over Active Bladder in Anesthetized Cystitis Rats] (Assay 5)

(1) Animals

Female Sprague-Dawley rats (180~250 g/Charles River Japan) were used. Cyclophosphamide (CYP) dissolved in saline was administered intra-peritoneally at 150 mg/kg 48 hours before experiment.

(2) Catheter Implantation

Rats were anesthetized by intraperitoneal administration of urethane (Sigma) at 1.25 g/kg. The abdomen was opened through a midline incision, and a polyethylene catheter (BECTON DICKINSON, PE50) was implanted into the bladder through the dome. In parallel, the inguinal region was incised, and a polyethylene catheter (BECTON DICKINSON, PE50) filled with saline (Otsuka) was inserted into a femoral vein. After the bladder was emptied, the rats were left for 1 hour for recovery from the operation.

(3) Cystometric Investigation

The bladder catheter was connected via T-tube to a pressure transducer (Viggo-Spectramed Pte Ltd, DT-XXAD) and a microinjection pump (TERUMO). Saline was infused at room temperature into the bladder at a rate of 3.6 ml/hr for 20 min. Intravesical pressure was recorded continuously on a chart pen recorder (Yokogawa). At least three reproducible micturition cycles, corresponding to a 20-minute period, were recorded before a test compound administration.

(4) Administration of Test Compounds

A testing compound dissolved in the mixture of ethanol, Tween 80 (ICN Biomedicals Inc.) and saline (1:1:8, v/v/v) was administered intravenously at 0.05 mg/kg, 0.5 mg/kg or 5 mg/kg. 3 min after the administration of the compound, saline (Nacalai Tesque) was infused at room temperature into the bladder at a rate of 3.6 ml/hr.

(5) Analysis of Cystometry Parameters

The cystometry parameters were analyzed as described previously [Lecci A et al: Eur. J. Pharmacol. 259: 129-135, 1994]. The micturition frequency calculated from micturition interval and the bladder capacity calculated from a volume of infused saline until the first micturition were analyzed from the cystometry data. The testing compounds-mediated inhibition of the frequency and the testing compounds-mediated increase of bladder capacity were: evaluated using unpaired Student's t-test. A probability levels less than 5% was accepted as significant difference. Data were analyzed as the mean±SEM from 4-7 rats.

[Measurement of Acute Pain]

Acute pain is measured on a hot plate mainly in rats. Two variants of hot plate testing are used: In the classical variant animals are put on a hot surface (52 to 56° C.) and the latency time is measured until the animals show nociceptive behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t, i.c.v., s.c., intradermal, transdermal) prior to pain testing.

[Measurement of Persistent Pain]

Persistent pain is measured with the formalin or capsaicin test, mainly in rats. A solution of 1 to 5% formalin or 10 to 100 µg capsaicin is injected into one hind paw of the experimental animal. After formalin or capsaicin application the animals show nociceptive reaction's like flinching, licking and biting of the affected paw. The number of nociceptive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

[Measurement of Neuropathic Pain]

Neuropathic pain is induced by different variants of unilateral sciatic nerve injury mainly in rats. The operation is performed under anesthesia. The first variant of sciatic nerve injury is produced by placing loosely constrictive ligatures around the common sciatic nerve (Bennett and Xie, Pain 33 (1988): 87-107). The second variant is the tight ligation of about the half of the diameter of the common sciatic nerve (Seltzer et al., Pain 43 (1990): 205-218). In the next variant, a group of models is used in which tight ligations or transections are made of either the L5 and L6 spinal nerves, or the L5 spinal nerve only (KIM S H; CHUNG J M, AN EXPERIMENTAL-MODEL FOR PERIPHERAL NEUROPATHY PRODUCED BY SEGMENTAL SPINAL NERVE LIGATION IN THE RA, PAIN 50 (3) (1992): 355-363). The fourth variant involves an axotomy of two of the three terminal branches of the sciatic nerve (tibial and common peroneal nerves) leaving the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynioa, as well as a thermal hyperalgesia. Mechanical allodynia is measured by means of a pressure transducer (electronic von Frey Anesthesiometer, IITC Inc.-Life Science Instruments,: Woodland Hills, SA, USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10° C. where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadanian rhytms in activity (Sudjo and Arndt, Universität zu Köln, Cologne, Germany), and by scoring differences in gait (foot print patterns; FOOTPRINTS program, Klapdor et al., 1997. A low cost method to analyse footprint patterns. J. Neurosci. Methods 75, 49-54).

Compounds are tested against sham operated and vehicle treated control groups. Substance application is performed at different time points via different application routes (i.v., i.p., p.o., i.t, i.c.v., s.c., intradermal, transdermal) prior to pain testing.

[Measurement of Inflammatory Pain]

Inflammatory pain is induced mainly in rats by injection of 0.75 mg carrageenan or complete Freund's adjuvant into one hind paw. The animals develop an edema with mechanical allodynia as well as thermal hyperalgesia. Mechanical allodynia is measured by means of a pressure transducer (electronic von Frey Anesthesiometer, IITC Inc.-Life Science Instruments, Woodland Hills, SA, USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hindpaws sectioned and weighed. The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.c.v., s.c., intradermal, transdermal) prior to pain testing.

[Measurement of Diabetic Neuropathic Pain]

Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.-Life Science Instruments, Woodland Hills, SA, USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

Results of $IC_{50}$ of capsaicin-induced $Ca^{2+}$ influx in the human VR1-transfected CHO cell line are shown in Examples and tables of the Examples below. The data corresponds to the compounds as yielded by solid phase synthesis and thus to levels of purity of about 40 to 90%. For practical reasons, the compounds are grouped in four classes of activity as follows:

$IC_{50}=A(<or=)0.1\ \mu M<B(<or=)0.5\ \mu M<C(<or=)1\ \mu M<D$

The compounds of the present invention also show excellent selectivity, and strong activity in other assays (2)-(5) described above.

Preparing Method of Starting Compounds

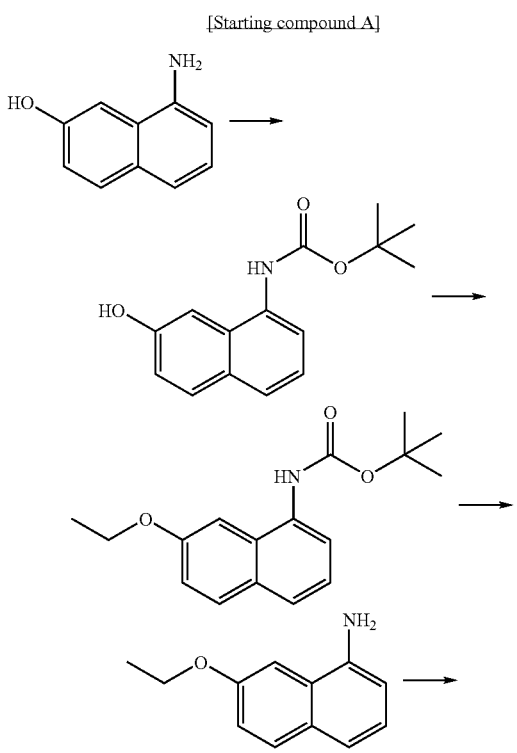

[Starting compound A]

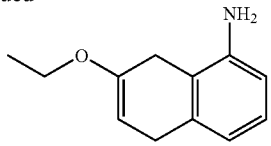

To a stirred solution of 8-amino-2-naphthol (50.0 g, 314 mmol) in tetrahydrofuran (1000 mL) was added di-t-butyldicarbonate (68.6 g, 314 mmol). The mixture was stirred at 70° C. for 18 hours. After the mixture was cooled to room temperature, solvent was removed under reduced pressure. To the residue was added ethylacetate, and washed with saturated aqueous solution of sodium carbonate and then with water. The extracted organic layer was dried over $Na_2SO_4$, filtered, and concentrated under reduced pressure. To the obtained residue was added diisopropyl ether, and the precipitate was filtered and dried to afford N-t-butoxycarbonyl-8-amino-2-naphthol (64.2 g, 79% yield).

MS (ESI) m/z 259 [M]+

$^1$H NMR (DMSO-d6) δ 1.48 (s, 9H), 7.07 (dd, J=2.2 Hz and 8.85 Hz, 1H), 7.20 (t, J=7.9 Hz, 1H), 7.24 (d, J =2.2 Hz, 1H), 7.36 (d, J=7.25 Hz, 1H), 7.60 (d, J=8.2 Hz, 1H), 7.75 (d, J=8.8 Hz, 1H), 8.92(s, 1H).

Next, to a mixture of N-t-butoxycarbonyl-8-amino-2-naphthol (64.0 g, 247 mmol) and Cesium carbonate (161 g, 493 mmol) in 300 mL anhydrous DMF was added iodoethane (42.3 g, 272 mmol) at room temperature. The mixture was stirred at 60° C. for 2 hours. Water was added to the mixture, and the product was extracted with ethylacetate. The organic layer was washed with water and brine, dried over $Na_2SO_4$, filtered, and concentrated under reduced pressure. To the obtained residue was added diisopropyl ether and the precipitate was collected and dried to afford (7-ethoxy-naphthalen-1-yl)-carbamic acid t-butyl ester (47.9 g, 67.5% yield).

MS (ESI) m/z 287[M]+

$^1$H NMR (DMSO-d6) δ 1.41 (t, J=6.95 Hz, 3H), 1.50 (s, 9H), 4.16 (q, J=6.95 Hz, 2H), 7.15 (dd, J=2.55 and 8.8 Hz, 1H), 7.28 (t, J=8.8 Hz, 1H), 7.36 (d, J=2.2 Hz, 1H), 7.54 (d, J=7.25 Hz, 1H), 7.61 (d, J=8.2 Hz, 1H), 7.80 (d, J=8.85 Hz, 1H), 9.12(s, 1H).

Next, to a (7-ethoxy-naphthalen-1-yl)-carbamic acid t-butyl ester (47.9 g, 167 mmol) in 100 mL anhydrous 1,4-dioxane was added 4N HCl in 1,4-dioxane (100 mL) at 0° C. The mixture was stirred at room temperature for 2 hours. Diisopropyl ether was added to the reaction mixture and the precipitate was filtered. To the obtained solid was added saturated sodium bicarbonate and the product was extracted with ethylacetate. The organic layer was dried over $Na_2SO_4$, filtered, and concentrated under reduced pressure to afford 7-ethoxy-naphthalen-1-ylamine (27.0 g, 86.3% yield).

MS (ESI) m/z 187 [M]+

$^1$H NMR (DMSO-d6) δ 1.39 (t, J 11.3 Hz, 3H), 4.15 (q, J=11.3 Hz, 2H), 5.52(s(br), 2H), 6.64 (dd, J=3.75 and 10.05 Hz, 1H), 7.01-7.07 (m, 3H), 7.39 (d, J=3.8 Hz, 1H), 7.63 (d, J=14.45 Hz, 1H).

Next, to a flask containing a mixture of 7-ethoxy-naphthalen-1-ylamine (1.80 g, 9.61mmol) and t-buthanol (2.13 g, 28.8 mmol) in tetrahydrofuran (20mL) was collected liquid ammonia (300 mL) at −78° C. To the mixture was added lithium (0.200 g, 28.8 mmol) over 30 minutes and stirred at −78° C. for 1 hour. Methanol and water was added, and the mixture was stirred at room temperature for 16 hours to allow ammonia to evaporate. To the obtained residue was added ethylacetate. The organic layer was washed with water, dried over Na$_2$SO$_4$, filtered, and concentrated under reduced pressure to afford 7-ethoxy-5,8-dihydronaphtalen-1-ylamine (1.37 g, 76% yield).

[Starting compound B]

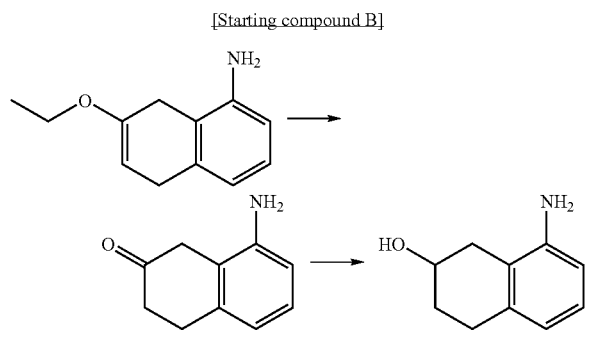

To a stirred solution of 7-ethoxy-5,8-dihydronaphthalen-1-ylamine (1.07 g, 5.65 mmol) in tetrahydrofuran (30 mL) was added solution of aqueous 2N HCl (10 mL), and stirred at 40° C. for 1 hour. The mixture was neutralized with addition of sodium bicorbonate, and the product was extracted with ethylacetate. The organic layer was washed with water, dried over Na$_2$SO$_4$, filtered, and concentrated under reduced pressure to afford 8-amino-3,4-dihydro-1H-naphthalen-2-one (0.71 g; 78% yield).

MS (ESI) m/z 162 [M+H]$^+$ $^1$H NMR (CDCl3) δ 2.62-2.65 (m, 2H), 3.07 (t, J=7.25 Hz, 2H), 3.34(s, 2H), 6.65 (d, J=7.85, -1H), 6.70 (d, J=7.25 Hz, 1H), 7.07 (t, J=7.55 Hz, 1H).

Next, to 8-amino-3,4-dihydro-1H-naphthalen-2-one (0.050 g, 0.318 mmol) in methanol (10 mL) was added sodium borohydride (0.030 g, 0.175 mmol) at 0° C., and the mixture was stirred for 1 hour. The mixture was poured into water, and the product was extracted with ethylacetate. The organic layer was dried over Na$_2$SO$_4$, filtered, and concentrated under reduced pressure to afford 8-amino-1,2,3,4-tetrahydro-naphthalen-2-ol (0.037 g, 71% yield).

MS (ESI) m/z 163 [M]$^+$ $^1$H NMR (DMSO-d6) δ 1.53-1.57 (m, 1H), 1.81-1.85 (m, 1H), 2.16 (dd, J=7.7 and 16.4 Hz, 1H), 2.61-2.74 (m, 3H), 3.89-3.90 (m, 1H), 4.65 (s, 2H), 4.72 (d, J=4.1 Hz, 1H), 6.28 (d, J=7.45 Hz, 1H), 6.28 (d, J=7.45 Hz, 1H), 6.41 (d, J=7.7 Hz, 1H), 6.76(t, J=7.55 Hz, 1H).

[Starting compound C]

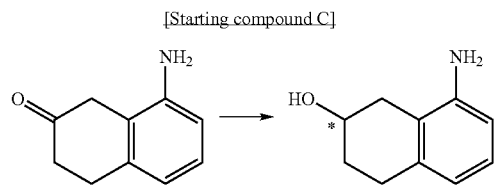

To a stirred solution benzeneruthenium(II) chloride dimer (3.16 mg, 0.006 mmol) and (1S, 2R)-(−)-cis-1-amino-2-indanol (3.7 mg, 0.025 mmol) in degaussed isopropanol was heated at 80° C. for 20 minutes under argon. The mixture was added to the solution of 8-amino-3,4-dihydro-1H-naphthalen-2-one (50 mg, 0.310 mmol) in isopropanol (3 mL) at room temperature. A solution of potassium hydroxide (3.48 mg, 0.062 mmol) in isopropanol (1 mL) was added, and the mixture was stiired at 45° C. for 1 hour. The rite was passed through silica gel and washed with ethylacetate. The filtrate was concentrated under reduced pressure to afford the chiral 8-amino-1,2,3,4-tetrahydro-naphthalen-2-ol enantiomer (33.0 mg, 65% yield).

MS (ESI) m/z 163 [M]$^+$ $^1$H NMR (DMSO-d6) δ 1.53-1.57 (m, 1H), 1.81-1.85 (m, 1H), 2.16 (dd, J=7.7 and 16.4 Hz, 1H) 2.61-2.74 (m, 3H), 3.89-3.90 (m, 1H), 4.65 (s, 2H), 4.72 (d, J=4.1 Hz, 1H), 6.28 (d, J=7.45 Hz, 1H), 6.28 (d, J=7.45 Hz, 1H), 6.41 (d, J=7.7 Hz, 1H), 6.76(t, J=7.55 Hz, 1H).

[Starting compound D]

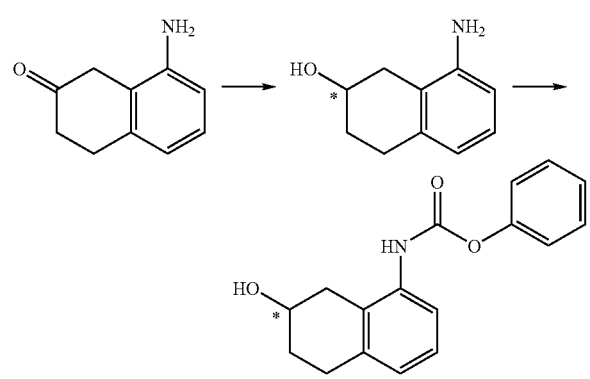

A stirred solution benzeneruthenium(II) chloride dimmer (1.55 g) and (1S, 2R)-(−)-cis-1-amino-2-indanol (1.85 g) in degassed isopropanol (500 ml) was heated at 80° C. for 20 minutes under argon, and then cooled to room temperature. The mixture was added to the solution of 8-amino-3,4-dihydro-1H-naphthalen-2-one (25.0 g) in isopropanol (700 ml) at room temperature followed by the prepared solution of potassium hydroxide (1.74 g) in 300 ml of isopropanol (pre-prepared at 45° C. to dissolve and then cooled to room temperature). After stirred at 45° C. for 30 minutes, the mixture was cooled to room temperature and was passed through silica gel pad and washed with ethylacetate. The filtrate was concentrated under reduced pressures and the obtained solid was dissolved in dichloromethane and treated with activated charcoal for 10 minutes. After filtered through a silica gel pad, the mixture was concentrated under reduced pressure. The obtained product was recrystallized from dichloromethane to afford red crystal, of (R)-8-amino-1,2,3,4-tetrahydro-naphthalen-2-ol (14 g, 56% yield).

MS (ESI) m/z 163 [M]$^+$ $^1$H NMR (DMSO-d6) δ 1.53-1.57 (m, 1H), 1.81-1.85 (m, 1H), 2.16 (dd, J=7.7 and 16.4 Hz, 1H), 2.61-2.74 (m, 3H), 3.89-3.90 (m, 1H), 4.65 (s, 2H), 4.72 (d, J=4.1 Hz, 1H), 6.28 (d, J=7.45 Hz, 1H), 6.28 (d, J=7.45 Hz, 1H), 6.41 (d, J=7.7 Hz, 1H), 6.76(t, J=7.55 Hz, 1H).

Use of (1R, 2S)-(+)-cis-1-amino-2-indanol resulted in of (S)-8-amino-1,2,3,4-tetrahydro-naphthalen-2-ol.

Next, a solution of (R)-8-amino-1,2,3,4-tetrahydro-naphthalen-2-ol -(36.2 g) and pyridine (18.8 ml) in THF (850 ml) cooled at 0° C. was added phenyl chloroformate (28.8 ml). The mixture was stirred for 3 hours at room temperature, and then poured into ethylacetate. The mixture was washed with aqueous NH$_4$Cl then with water, and the organic layer was dried over Na$_2$SO$_4$, filtered, and concentrated under reduced pressure. To the obtained residue was added acetonitrile, and the precipitates were collected and washed with a mixture of acetonitrile and diisopropyl ether (2:3) to obtain {(R)-7-Hydroxy-5,6,7,8-tetrahydro-naphthalen-1-yl}carbamic acid phenyl ester (33.0 g).

MS (ESI) m/z 284 [M+H]+

¹H NMR (DMSO-d6) δ 1.59-1.64 (m, 1H),1.83-1.89 (m, 1H), 2.68-2.99 (m, 4H), 3.90-3.92 (m, 1H), 4.84 (dd, J=3.8 Hz and 29.9 Hz, 1H), 6.75 (d, J=7.9 Hz, 1H), 7.07-7.25(m 6H), 7.42 (t, J=7.85 Hz, 1H), 9.29(s, 1H).

Example 1-1

N-[4-chloro-3-(trifluoromethyl)phenyl]-N'-(7-hydroxy-5,6,7,8-tetrahydro-1-naphthalenyl)urea

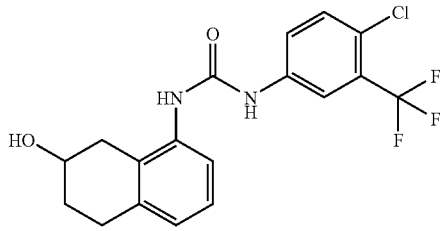

This example was performed according to the general method F.

To a stirred solution of 7-ethoxy-5,8-dihydronaphthalen-1-ylamine (0.16 g, 0.84mmol) in tetrahydrofuran (15 mL) was added 4-chloro-3-trifluoromethyl-phenylisocyanate (0.22 g, 1.0 mmol). The mixture was stirred at room temperature for 1.5 hours and was poured into water. The product was extracted with ethylacetate, and the organic layer was dried over Na₂SO₄, filtered, and concentrated under reduced pressure to afford N-(4-chloro-3-trifluoromethyl-phenyl)-N'-(7-ethoxy-5,8-dihydro-naphthalen-1-yl)urea (0.31 g, 89% yield). Next, to a solution of N-(4-chloro-3-trifluoromethyl-phenyl)-N'-(7-ethoxy-5,8-dihydro-naphthalen 1-yl)-urea (0.21 g, 0.51 mmol) in tetrahydrofuran (20 mL) was added a solution of aqueous 1N hydrochloric acid (5 mL), and the mixture was stirred at 40° C. for 45 minutes. The mixture was neutralized with addition of 10% aqueous sodium bicarbonate solution, and extracted with ethylacetate. The organic layer was dried over Na₂SO₄, filtered, and concentrated under reduced pressure to afford N(4-chloro-3-tri-fluoromethyl-phenyl)-N'-(7-oxo-5,6,7,8-tetrahydro-naphthalen-1-yl)urea (0.16 g, 85% yield). Next, to N-(4-chloro-3-trifluoromethyl-phenyl)-N'-7-oxo-5,6,7,8-tetrahydro-naphthalen-1-yl)urea (0.07 g, 0.18 mmol) in methanol (10 mL) was added sodium borohydride (0.04 g, 0.09 mmol) at 0° C., and the mixture was stirred for 30 minutes. The mixture was poured into water, and the product was extracted with ethylacetate. The organic layer was dried over Na₂SO₄, filtered, and concentrated under reduced pressure, and the obtained product was recrystalized from a mixture of ethylacetate/hexane (1/2) solution to give N-[4chloro-3-(trifluoromethyl)phenyl]-N'-(7-hydroxy-5,6,7,8-tetrahydro-1-naphthalenyl)urea (41 mg, 59% yield)

¹H NMR (DMSO-d6) δ 1.57-1.58 (m, 1H),1.87-1.90 (m, 1), 2.36-2.42 (m, 1H), 2.63-2.76 (m, 1H), 2.83-2.87 (m, 2H), 3.91-3.96 (m, 1H), 4.87 (d, J=4.1 Hz, 1H), 6.82 (d, J=7.6 Hz, 1H), 7.06 (t, J=7.6 Hz, 1H), 7.58 (d, J=7.6 Hz, 1H), 7.61-7.62 (m, 2H), 7.93 (s, 1H), 8.09 (s, 1H), 9.47 (s, 1H).

Molecular weight: 384:8

MS (M+H): 384 mp: 227-228° C.

In vitro activity class: A

Example 1-2

N-[4-chloro-3-(trifluoromethyl)phenyl]-N'-{(R)-7-hydroxy-5,6,7,8-tetrahydro-1-naphthalenyl}urea

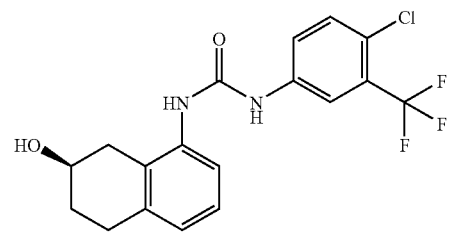

A racemic mixture of N-[4-chloro-3-(trifluoromethyl)phenyl]-N'-(7-hydroxy-5,6,7,8-tetrahydro-1-naphthalenyl)urea (30.0 mg) was separated by chiral HPLC (Daicel OD column, n-hexane: 2-propanol=98:2) to the corresponding R-isomer (8.3 mg). Chiral HPLC (ChiralCel OD 0.49 cm×25 cm column, n-hexane/ethanol=97/3, flow rate 1.5 mL/min) R-isomer was detected at 20.1 minutes.

Molecular weight: 384.8

MS (M+H): 384

Example 1-3

N-[4-chloro-3-(trifluoromethyl)phenyl]-N'-{(S)-7.-hydroxy-5,6,7,8-tetrahydro-1-naphthalenyl}urea

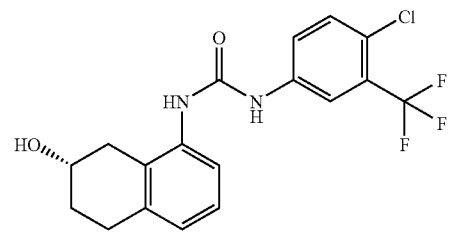

A racemic mixture of N-[4-chloro-3-(trifluoromethyl)phenyl]-N'-(7-hydroxy-5,6,7,8-tetrahydro-1-naphthalenyl)urea (30.0 mg) was separated by chiral HPLC (Daicel OD column, n-hexane: 2-propanol=98:2) to the corresponding S-isomer (2.2 mg). Chiral HPLC (ChiralCel OD 0.49 cm ×25 cm column, n-hexane/ethanol 97/3, flow rate 1.5 mL/min) S-isomer was detected at 17.6 minutes.

Molecular weight: 384.8

MS (M+H): 384

Example 2-1

N-phenyl-N'-(7-hydroxy-5,6,7,8-tetrahydro-1-naphthalenyl) urea

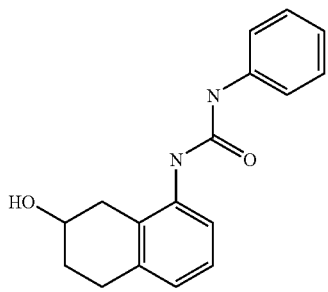

This example was performed according to the general method A.

To a solution of 8-amino-1,2,3,4-tetrahydro-naphthalen-2-ol (20.0 mg, 0.123 mmol) in 1,4-dioxane (1.0 mL) was added phenyl isocyanate. (14.6 mg, 0.123 mmol) at room temperature. The mixture was stirred for 16 hours, and then added diisopropyl ether and hexane. The precipitate was filtered and dried to give N-phenyl-N'-(7-hydroxy-5,6,7,8-tetrahydro-1-naphthalenyl)urea (17.8 mg, 51% yield).

Molecular weight: 282.3

MS (M+H): 283 mp: 198-199° C.

Activity class: C

With the use of the starting material B and according to procedures similar to the examples 2-1 above, the compounds in Example 2-2 to 2-41 were synthesized and tested.

TABLE 1

| Ex no | MOLSTRUCTURE | MW | MS | MP | activity class |
|---|---|---|---|---|---|
| 2-2 | | 316,79024 | 317 | 197-199 | B |
| 2-3 | | 316,79024 | 317 | 216-218 | A |
| 2-4 | | 316,79024 | 317 | 229-231 | A |

TABLE 1-continued

| Ex no | MOLSTRUCTURE | MW | MS | MP | activity class |
|---|---|---|---|---|---|
| 2-5 | | 312,3717 | 313 | 187-189 | B |
| 2-6 | | 312,3717 | 313 | 213-215 | D |
| 2-7 | | 350,34359 | 351 | 217-219 | C |
| 2-8 | | 350,34359 | 351 | 227-228 | A |
| 2-9 | | 350,34359 | 351 | 222-224 | A |

TABLE 1-continued

| Ex no | MOLSTRUCTURE | MW | MS | MP | activity class |
|---|---|---|---|---|---|
| 2-10 | (ethyl 2-{[(7-hydroxy-5,6,7,8-tetrahydronaphthalen-1-yl)carbamoyl]amino}benzoate) | 354,40934 | 355 | 178-180 | D |
| 2-11 | (ethyl 3-{[(7-hydroxy-5,6,7,8-tetrahydronaphthalen-1-yl)carbamoyl]amino}benzoate) | 354,40934 | 355 | 176-178 | A |
| 2-12 | (ethyl 4-{[(7-hydroxy-5,6,7,8-tetrahydronaphthalen-1-yl)carbamoyl]amino}benzoate) | 354,40934 | 355 | 204-206 | A |
| 2-13 | (1-(7-hydroxy-5,6,7,8-tetrahydronaphthalen-1-yl)-3-(naphthalen-1-yl)urea) | 332,40575 | 333 | 250-252 | A |

TABLE 1-continued

| Ex no | MOLSTRUCTURE | MW | MS | MP | activity class |
|---|---|---|---|---|---|
| 2-14 | | 332,40575 | 333 | 212-214 | A |
| 2-15 | | 300,33564 | 301 | 214-216 | B |
| 2-16 | | 361,24124 | 362 | 237-239 | A |
| 2-17 | | 351,23527 | 352 | 234-235 | A |
| 2-18 | | 296,3723 | 297 | 198-200 | B |

TABLE 1-continued

| Ex no | MOLSTRUCTURE | MW | MS | MP | activity class |
|---|---|---|---|---|---|
| 2-19 | | 324,42648 | 325 | 186-188 | A |
| 2-20 | | 374,44339 | 375 | 188-190 | A |
| 2-21 | | 325,41406 | 326 | 206-207 | D |
| 2-22 | | 296,3723 | 297 | 198-200 | B |
| 2-23 | | 310,39939 | 311 | 224-226 | B |

TABLE 1-continued

| Ex no | MOLSTRUCTURE | MW | MS | MP | activity class |
|---|---|---|---|---|---|
| 2-24 | 3-methylbenzyl urea of 7-hydroxy-tetrahydronaphthalen-1-yl | 310,39939 | 311 | 194-196 | B |
| 2-26 | 4-methylbenzyl urea of 7-hydroxy-tetrahydronaphthalen-1-yl | 310,39939 | 311 | 230-232 | A |
| 2-27 | 2-fluorobenzyl urea of 7-hydroxy-tetrahydronaphthalen-1-yl | 314,36273 | 315 | 184-187 | B |
| 2-28 | 3-fluorobenzyl urea of 7-hydroxy-tetrahydronaphthalen-1-yl | 314,36273 | 315 | 193-194 | B |
| 2-29 | 4-fluorobenzyl urea of 7-hydroxy-tetrahydronaphthalen-1-yl | 314,36273 | 315 | 218-221 | A |
| 2-30 | 2-chlorobenzyl urea of 7-hydroxy-tetrahydronaphthalen-1-yl | 330,81733 | 331 | 213-215 | B |

TABLE 1-continued

| Ex no | MOLSTRUCTURE | MW | MS | MP | activity class |
|---|---|---|---|---|---|
| 2-31 | | 326,39879 | 327 | 209-211 | B |
| 2-32 | | 310,39939 | 311 | 161-163 | C |
| 2-33 | | 234,30061 | 235 | 216-217 | D |
| 2-34 | | 282,34521 | 283 | 198-199 | C |
| 2-35 | | 316,79024 | 317 | 197-199 | B |

TABLE 1-continued
| Ex no | MOLSTRUCTURE | MW | MS | MP | activity class |
|---|---|---|---|---|---|
| 2-36 | 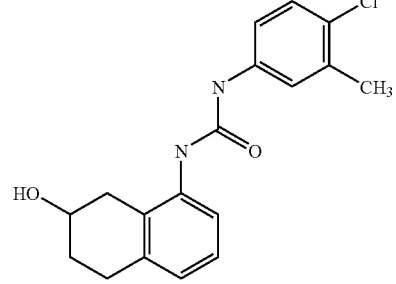 | 330,81733 | 331 | >180Z | A |
| 2-37 | 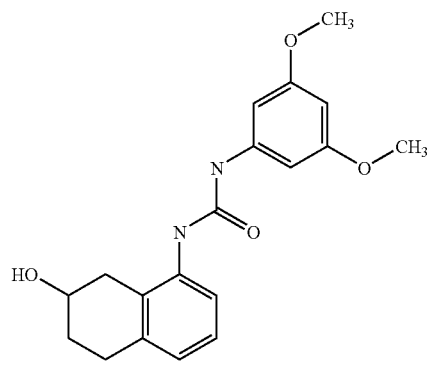 | 342,39819 | 343 | >150Z | A |
| 2-38 | 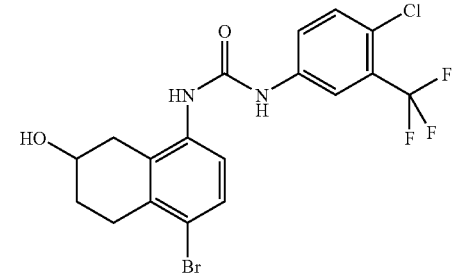 | 463,68465 | 464 | 234-235 | A |
| 2-39 | 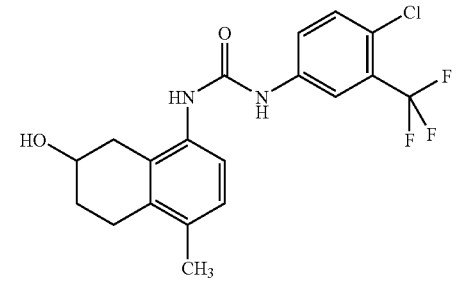 | 398,81 | 399 | 219-220 | A |
| 2-40 | 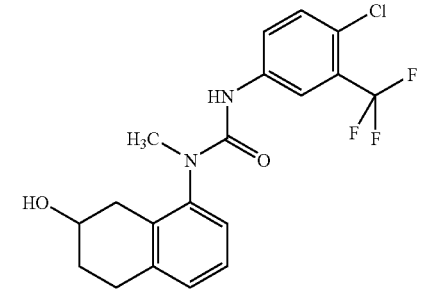 | 398,81571 | 399 | 136-137 | B |

TABLE 1-continued

| Ex no | MOLSTRUCTURE | MW | MS | MP | activity class |
|---|---|---|---|---|---|
| 2-41 | | 398.81571 | 399 | 213 | B |

Example 3-1

N-(4-chloro-3-(trifluoromethyl)phenyl)N'-(7-hydroxy-5,6,7,8-tetrahydro-1-naphthalenyl)urea chiral enantiomer This example was performed according to the general method G.

To a solution of chiral 8-amino-1,2,3,4-tetrahydro-naphthalen-2-ol enantiomer (33.0 mg, 0.202 mmol) in 1,4-dioxane (3.0 mL) was added 4-chloro-3-trifluoro-methyl-phenylisocyanate (44.8 mg, 0.202 mmol) at room temperature. The mixture was stirred for 16 hours, and then added diisopropyl ether and hexane. The precipitate was filtered and dried to give chiral N-(4-chloro-3-(trifluoro methyl)-phenyl)-N'-(7-hydroxy-5,6,7,8-tetrahydro-1-naphthalenyl)urea (54.0 mg, 69% yield). Enantiomeric excess (% ee) was measured by using Chiral Cel OD column (15% isopropanol in hexane as eluent with 1 mL per minutes).

Molecular weight: 384.8
MS (M+H): 384
mp: 227-228° C.
In vitro activity class: A

Example 4-1

N-(7-hydroxy-5,6,7,8-tetrahydro-naphthalen-1-yl)-N'-(4-trifluoromethoxy-benzyl)-urea

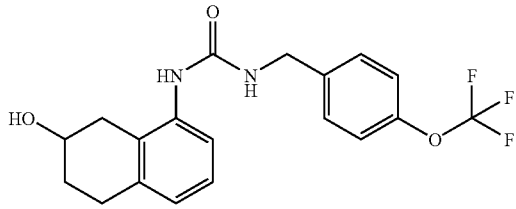

This example was performed according to the general method C.

A mixture of 7-hydroxy-5,6,7,8-tetrahydro-naphthalen-1-yl)-carbamic acid phenyl ester (30.0 mg, 0.11. mmol) and 4-trifluoromethoxy-benzylamine (21.3 mg, 0.11 mmol) in DMSO (1.0 ml) was stirred at 100° C. for 17 hours. The reaction mixture was cooled to room temperature, and water was added. Precipitates were filtered and washed with water then with acetonitrile to obtain N-(7-hydroxy-5,6,7,8-tetrahydro-naphthalen-1-yl)-N'-(4-trifluoromethoxy-benzyl)-urea (6.70 mg, 17% yield).

$^1$H NMR (DMSO-$d_6$) δ 1.54-1.65 (m, 1H), 1.81-1.92 (m, 1H), 2.25-2.38 (m, 1H), 2.68-2.88 (m, 3H), 3.86-3.98 (m, 1H), 4.32 (d, J=6.0 Hz, 2H), 4.85 (d, J=4.1 Hz, 1H), 6.72 (d, J=7.5 Hz, 1H), 6.98 (t, J=7.5 Hz, 1H), 7.06 (t, J=6.0 Hz, 1H), 7.34 (d, J=8.3 Hz, 2H), 7.43 (d, J=8.3 Hz, 2H), 7.63 (d, J=7.5 Hz, 1H), 7.5 (s, 1H).

Molecular weight: 380.36
MS (M+H): 381
mp: 213° C.
In vitro activity class: A

Example 4-2

N-{(R)-7-hydroxy-5,6,7,8-tetrahydro-naphthalen-1-yl}-N'-(4-trifluoromethoxy-benzyl)-urea

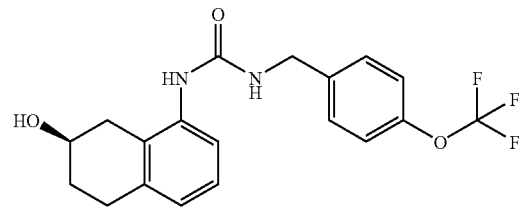

This example was performed according to the general method C.

A mixture of (R)-7-hydroxy-5,6,7,8-tetrahydro-naphthalen-1-yl)-carbamic acid phenyl ester (147.3 mg, 0.52 mmol) and 4-trifluoromethoxy-benzylamine (99.4 mg, 0.52 mmol) in DMSO (1.5 ml) was stirred at 150° C. for 1.5 hours. The reaction mixture was cooled to room temperature, and ethylacetate and water were added. The extracted organic layer was washed with water then brine, dried over $Na_2SO_4$, filtered and concentrated under reduced pressure. The obtained residue was triturated with dichloromethane and hexane to obtain N-{(R)-7-hydroxy-5,6,7,8-tetrahydro-naphthalen-1-yl}-N'-(4-trifluoromethoxy-benzyl)-urea (168.0 mg, 85% yield).

$^1$H NMR (DMSO-$d_6$) δ 1.54-1.65 (m, 1H), 1.81-1.92 (m, 1H), 2.25-2.38 (m, 1H), 2.68-2.88 (m, 3H), 3.86-3.98 (m, 1H), 4.32 (d, J=6.0 Hz, 2H), 4.85 (d, J=4.1 Hz, 1H), 6.72 (d, J=7.5 Hz, 1H), 6.98 (t, J=7.5 Hz, 1H), 7.06 (t, J=6.0 Hz, 1H), 7.34 (d, J=8.3 Hz, 2H), 7.43 (d, J=8.3 Hz, 2H), 7.63 (d, J=7.5 Hz, 1H), 7.5 (s, 1H).

Molecular weight: 380.36
MS (M+H): 381
In vitro activity class: A
Chiral HPLC (ChiralCel AD 0.49 cm×25 cm column, n-hexane/ethanol 90/10, flow rate 1.5 mL/min) R-isomer was detected at 17.7 minutes.

Example 4-3

N-{(S)-7-hydroxy-5,6,7,8-tetrahydro-naphthalen-1-yl}-N'-(4-trifluoromethoxy-benzyl)-urea

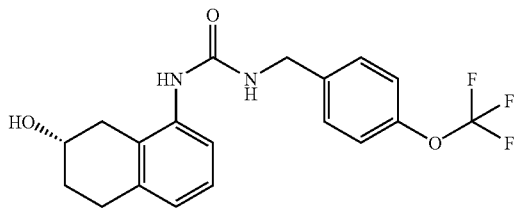

This example was performed according to the general method C.

A mixture of (S)-7-hydroxy-5,6,7,8-tetrahydro-naphthalen-1-yl)-carbamic acid phenyl ester (85.0 mg, 0.30 mmol) and 4trifluoromethoxy-benzylamine (57.4 mg, 0.30 mmol) in DMSO (1.0 ml) was stirred at 150° C. for 1.5 hours. The reaction mixture was cooled to room temperature, and ethylacetate and water were added. The extracted organic layer was washed with water then brine, dried over $Na_2SO_4$, filtered and concentrated under reduced pressure. The obtained residue was triturated with dichloromethane and hexane to obtain N-{(S)-7-hydroxy-5,6,7,8-tetrahydro-naphthalen-1-yl}-N'-(4-trifluoromethoxy-benzyl)-urea (95.0 mg, 83% yield).

$^1$H NMR (DMSO-$d_6$) δ 1.54-1.65 (m, 1H), 1.81-1.92 (m, 1H), 2.25-2.38 (m, 1H), 2.68-2.88 (m, 3H), 3.86-3.98 (m, 1H), 4.32 (d, J=6.0 Hz, 2H), 4.85 (d, J=4.1 Hz, 1H), 6.72 (d, J=7.5 Hz, 1H), 6.98 (t, J=7.5 Hz, 1H), 7.06 (t, J=6.0 Hz, 1H), 7.34 (d, J=8.3 Hz, 2H), 7.43 (d, J=8.3 Hz, 2H), 7.63 (d, J=7.5 Hz, 1H), 7.5 (s, 1H).

Molecular weight: 380.36
MS (M+H): 381
In vitro activity class: A

Chiral HPLC (ChiralCel AD 0.49 cm×25 cm column, n-hexane/ethanol=90/10, flow rate 1.5 mL/min) S-isomer was detected at 13.2 minutes.

Example 4-4

N-{(R)-7-hydroxy-5,6,7,8-tetrahydro-naphthalen-1-yl}-N'-(4-trifluoromethyl-benzyl)-urea

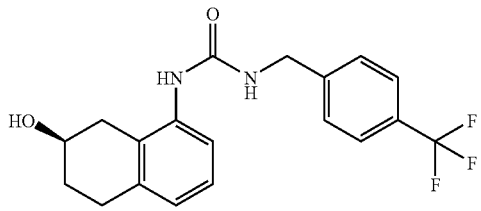

This example was performed according to the general method C.

A mixture of (R)-7-hydroxy-5,6,7,8-tetrahydro-naphthalen-1-yl)carbamic acid phenyl ester (150.0 mg, 6.53 mmol) and 4-trifluoromethyl-benzylamine (92.7 mg, 0.53 mmol) in DMSO (2.0 ml) was stirred at 100° C. for 1.5 hours. The reaction mixture was cooled to room temperature, and ethylacetate and water were added. The extracted organic layer was washed with water then brine, dried over $Na_2SO_4$, filtered and concentrated under reduced pressure. The obtained residue was triturated with dichloromethane and hexane to obtain N-{(R)-7-hydroxy-5,6,7,8-tetrahydro-naphthalen-1-yl}-N'-(4-trifluoromethyl-benzyl)-urea (156 mg, 81% yield).

$^1$H NMR (DMSO-d6) δ 1.58-1.59 (m, 1H),1.85-1.86 (m, 1H), 2.33-2.85 (m, 4H), 3.91-3.92 (m, 1H), 4.39 (d, J=5.7 Hz, 2H), 4.84 (d, J=4.1 Hz, 1H), 6.72 (d, J=7.25 Hz, 1H), 6.98(t, J=7.9 Hz, 1H), 7.12(t, J=6.0 Hz, 1H), 7.51-7.71(m, 6H).

Molecular weight: 364.37
MS (M+H): 366
mp: 204.3° C.
In-vitro activity class: A

Chiral HPLC (ChiralCel AD 0.49 cm×25 cm column, n-hexane/ethanol=90/10, flow rate 1.5 ml/min) R-isomer was detected at 16.2 minutes.

Example 4-5

N-{(S)-7-hydroxy-5,6,7,8-tetrahydro-naphthalen-1-yl}-N'-(4-trifluoromethyl-benzyl)-urea

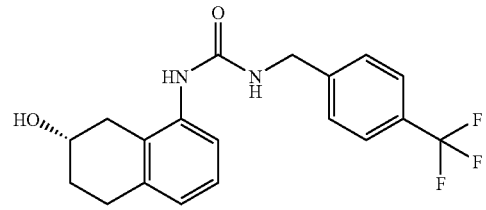

This example was performed according to the general method C.

A mixture of (S)-7-hydroxy-5,6,7,8-tetrahydro-naphthalen-1-yl)carbamic acid phenyl ester (100.0 mg, 0.35 mmol) and 4-trifluoromethyl-benzylamine (61.8 mg, 0.35 mmol) in DMSO (1.5 ml) was stirred at 100° C. for 1.5 hours. The reaction mixture was cooled to room temperature, and ethylacetate and water were added. The extracted organic layer was washed with water then brine, dried over $Na_2SO_4$, filtered and concentrated under reduced pressure. The obtained residue was triturated with dichloromethane and diisopropyl ether to obtain N-{(S)-7-hydroxy-5,6,7,8-tetrahydro-naphthalen-1-yl}-N'-(4-trifluoromethyl-benzyl)-urea (109 mg, 85% yield).

$^1$H NMR (DMSO-d6) δ 1.58-1.59 (m, 1H), 1.85-1.86 (m, 1H), 2.33-2.85 (m, 4H), 3.91-3.92 (m, 1H), 4.39 (d, J=5.7 Hz, 2H), 4.84 (d, J=4.1 Hz, 1H), 6.72 (d, J=7.25 Hz, 1H), 6.98(t, J=7.9 Hz, 1H), 7.12(t, J=6.0 Hz, 1H), 7.51-7.7(m, 6H).

Molecular weight: 364.37
MS (M+H): 366
In vitro activity class: A

Chiral HPLC (ChiralCel AD 0.49 cm×25 cm column, n-hexane/ethanol=90/10, flow rate 1.5 mL/min) S-isomer was detected at 11.7 minutes.

In a similar method according to the Example 4-1, 4-2, 4-3, 4-4 and 4-5 above, the compounds in Example 4-6 to 4-54 were synthesize.

TABLE 2

| No. | MOLSTRUCTURE | MW | MS (M + H) | MP | activity class |
|---|---|---|---|---|---|
| 4-6 | | 296,3723 | 297 | 198-200 | B |
| 4-7 | | 375,26833 | 376 | 220.5-222 | A |
| 4-8 | | 364,37068 | 365 | 186-187 | A |
| 4-9 | | 330,81733 | 331 | 235 Z | A |
| 4-10 | | 364,37068 | 365 | 169,9 | A |

TABLE 2-continued

| No. | MOLSTRUCTURE | MW | MS (M + H) | MP | activity class |
|---|---|---|---|---|---|
| 4-11 | | 326,39879 | 327 | 196 | B |
| 4-12 | | 332,35316 | 333 | 193,4 | A |
| 4-13 | | 326,39879 | 327 | 171,3 | B |
| 4-14 | | 330,81733 | 331 | 188,7 | A |
| 4-15 | | 365,26236 | 366 | 212,7 | A |
| 4-16 | | 352,48066 | 353 | 199,9 | A |

TABLE 2-continued

| No. | MOLSTRUCTURE | MW | MS (M + H) | MP | activity class |
|---|---|---|---|---|---|
| 4-17 | | 380,37008 | 381 | 213 | A |
| 4-18 | | 365,26236 | 366 | 201,4 | A |
| 4-19 | | 364,37068 | 365 | 218,6 | A |
| 4-20 | | 356,42528 | 357 | 212 | B |
| 4-21 | | 375,26833 | 376 | 206,4 | A |

TABLE 2-continued

| No. | MOLSTRUCTURE | MW | MS (M + H) | MP | activity class |
|---|---|---|---|---|---|
| 4-22 | | 354,40934 | 355 | 210,9 | A |
| 4-23 | | 386,45177 | 387 | 175,4 | C |
| 4-24 | | 375,26833 | 376 | 164,2 | A |
| 4-25 | | 341,36983 | 342 | 216,3 | A |
| 4-26 | | 432,36906 | 433 | 200,3 | A |

TABLE 2-continued

| No. | MOLSTRUCTURE | MW | MS (M + H) | MP | activity class |
|---|---|---|---|---|---|
| 4-27 | | 356,42528 | 357 | 219,7 | C |
| 4-28 | | 332,35316 | 333 | 140,2 | C |
| 4-29 | | 380,37008 | 381 | 149 | A |
| 4-30 | | 340,38225 | 341 | 278,5 | C |
| 4-31 | | 311,38697 | 312 | 223 | C |

TABLE 2-continued

| No. | MOLSTRUCTURE | MW | MS (M + H) | MP | activity class |
|---|---|---|---|---|---|
| 4-32 | | 311,38697 | 312 | 132,5 | C |
| 4-33 | | 368,43643 | 369 | 209,5 | B |
| 4-34 | | 339,44115 | 340 | 197.7-199.5 | A |
| 4-35 | | 398,81571 | 399 | 187,5 | A |
| 4-36 | | 344,84442 | 345 | >200 | A |
| 4-37 | | 382,36111 | 383 | 174 | A |

TABLE 2-continued

| No. | MOLSTRUCTURE | MW | MS (M + H) | MP | activity class |
|---|---|---|---|---|---|
| 4-38 | | 388,47048 | 389 | 181-183 | A |
| 4-39 | | 408,88842 | 409 | 199-201 | A |
| 4-40 | | 366,34299 | 367 | 198-200 | A |
| 4-41 | | 328,38982 | 329 | 163-164 | B |
| 4-42 | | 389,29542 | 389-391 | 174 | A |

TABLE 2-continued

| No. | MOLSTRUCTURE | MW | MS (M + H) | MP | activity class |
|---|---|---|---|---|---|
| 4-43 | | 372,47108 | 373 | 205-206 | C |
| 4-44 | | 358,87151 | 359 | 140-141 | B |
| 4-45 | | 396,43468 | 397 | 209,1 | A |
| 4-46 | | 346,43284 | 347 | 221,1 | A |
| 4-47 | | 321,38218 | 322 | 147 decomp. | B |

TABLE 2-continued

| No. | MOLSTRUCTURE | MW | MS (M + H) | MP | activity class |
|---|---|---|---|---|---|
| 4-48 | | 310,39939 | 311 | 169,6 | B |
| 4-49 | | 360,45993 | 361 | 137,4 | A |
| 4-50 | | 375,44977 | 376 | >200 decomp. | C |
| 4-51 | | 447,50486 | 448 | 159 | A |
| 4-52 | | 483,96583 | 448 | 83 | A |

TABLE 2-continued

| No. | MOLSTRUCTURE | MW | MS (M + H) | MP | activity class |
|---|---|---|---|---|---|
| 4-53 | Chiral | 344,84442 | 345 | 173,9 | A |
| 4-54 | Chiral | 344,84442 | 345 | 159,3 | A |

Example 4-48

N-[(7R)-7-hydroxy-5,6,7,8-tetrahydro-1-naphthalenyl]-N'-{2-[4-(trifluoromethyl)phenyl]-ethyl}urea

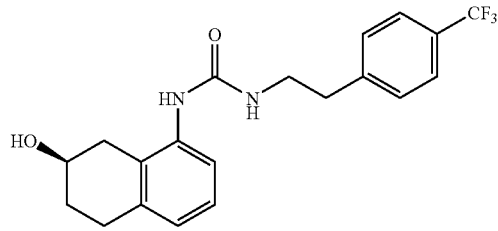

This example was performed according to the general method C.

A mixture of 7-hydroxy-5,6,7,8-tetrahydro-naphthalen-1-yl)-carbamic acid phenyl ester (10.0 mg, 0.35 mmol) and 2-(4-trifluoromethyl-phenyl)ethylamine (66.7 mg, 0.35 mmol) in DMSO (1.0 ml) was stirred at 60° C. for 3 hours. The reaction mixture was cooled to room temperature, and the mixture was partitioned between water and ethyl acetate. The organic layer was dried over $Na_2SO_4$ and evaporated to dryness. The raw material was stirred with diethyl ether, and the precipitate was filtered and dried in vacuo to give N-[(7R)-7-hydroxy-5,6,7,8-tetrahydro-1-naphthalenyl]-N'-{2-[4-(trifluoromethyl)phenyl]ethyl}urea (125 mg, 94% yield).

$^1$H NMR (DMSO-$d_6$) δ 1.45-1.68. (m, 1H), 1.78-1.93 (m, 1H), 2.29 (dd, 1H), 2.65-2.93 (m, 5H), 3.39 (dt, 2H), 3.80-4.00 (m, 1H), 4.88 (d, 1H), 6.57 (t, 1H), 6.70 (d, 1H), 6.98 (t, 1H), 7.42-7.75 (m, 6H).

Molecular weight: 378.39

MS (M+H): 379

Example 4-49

N-[(7R)-7-hydroxy-5,6,7,8-tetrahydro-1-naphthalenyl]-N'-{2-[4-(trifluoromethoxy)phenyl]-ethyl}urea

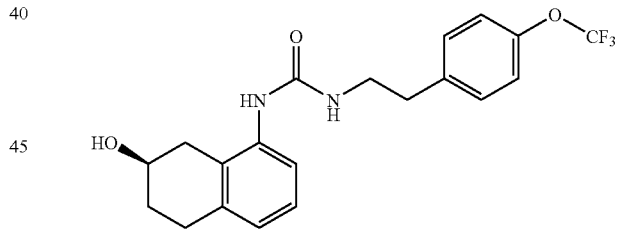

This example was performed according to the general method C.

A mixture of 7-hydroxy-5,6,7,8-tetrahydro-naphthalen-1-yl)-carbamic acid phenyl ester (100 mg, 0.35 mmol) and 2-(4-trifluoromethoxy-phenyl)ethylamine (72.4 mg, 0.35 mmol) in DMSO (1.0 ml) was stirred at 60° C. for 2.5 hours. The reaction mixture was cooled to room temperature, and the mixture was partitioned between water and ethyl acetate. The organic layer was dried over $Na_2SO_4$ and evaporated to dryness. The raw material was stirred with diethyl ether, and the precipitate was filtered and dried in vacuo to give N-[(7R)-7-hydroxy-5,6,7,8-tetrahydro-1-naphthalenyl]-N'-{2-[4-(trifluoromethoxy)phenyl]ethyl}urea (109 mg, 79% yield).

$^1$H NMR (DMSO-$d_6$) δ 1.50-1.65 (m, 1H), 1.80-1.91 (m, 1H), 2.30 (dd, 1H), 2.60-2.88 (m, 5H), 3.34 (dt, 2H), 3.85-3.97 (m, 1H), 4.81 (d, 1H), 6.55 (t, 1H), 6.70 (d, 1H), 6.98 (t, 1H), 7.30 (d, 2H), 7.38 (d, 2H), 7.50 (s, 1H), 7.59 (d, 1H).

Molecular weight: 394.39

MS (M+H): 395

TABLE 3
| No. | MOLSTRUCTURE | MW | MS (M + H) | MP | activity class |
|---|---|---|---|---|---|
| 5-2 | 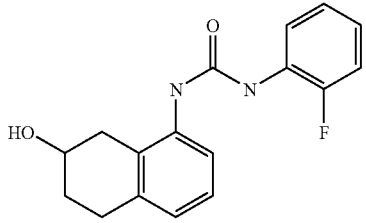 | 300,336 | 301 | | C |
| 5-3 | 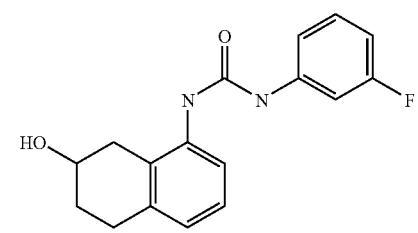 | 300,336 | 301 | 204-205 | B |
| 5-4 | 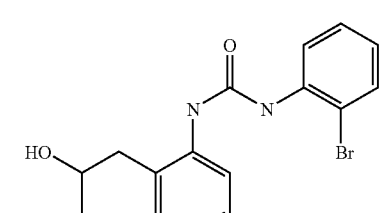 | 361,241 | 362 | 196-197 | B |
| 5-5 | 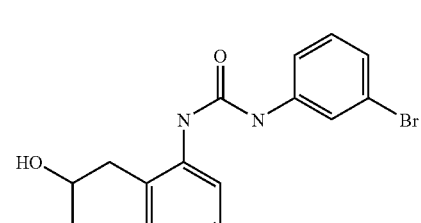 | 361,241 | 362 | | A |
| 5-6 | 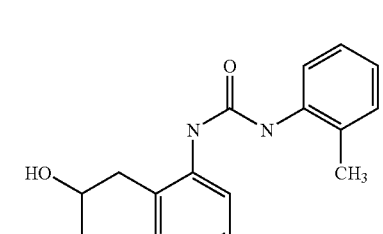 | 296,372 | 297 | 223 | C |
| 5-7 | 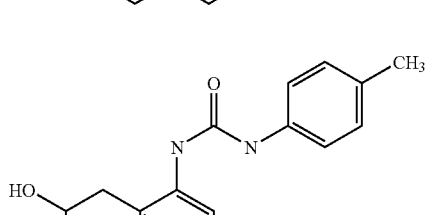 | 296,372 | 297 | | B |

TABLE 3-continued

| No. | MOLSTRUCTURE | MW | MS (M + H) | MP | activity class |
|---|---|---|---|---|---|
| 5-8 | | 324,426 | 325 | | A |
| 5-9 | | 338,454 | 339 | | A |
| 5-10 | | 374,443 | 375 | 194-195 | A |
| 5-11 | | 366,343 | 367 | 203-204 | A |
| 5-12 | | 380,37 | 381 | | A |
| 5-13 | | 408,242 | 409 | 226-228 | A |

TABLE 3-continued

| No. | MOLSTRUCTURE | MW | MS (M + H) | MP | activity class |
|---|---|---|---|---|---|
| 5-14 | | 326.399 | 327 | >192Z | A |
| 5-15 | | 328.371 | 329 | >82Z | C |
| 5-16 | | 328.436 | 329 | >186Z | B |
| 5-17 | | 330.362 | 331 | >185Z | A |
| 5-18 | | 342.398 | 313 | 203-212 | B |

TABLE 3-continued

| No. | MOLSTRUCTURE | MW | MS (M + H) | MP | activity class |
|---|---|---|---|---|---|
| 5-19 | | 346,817 | 347 | >200Z | A |
| 5-20 | | 298,345 | 299 | >202Z | C |
| 5-21 | | 310,399 | 311 | >223Z | A |
| 5-22 | | 310,399 | 311 | >197Z | A |
| 5-23 | | 310,399 | 311 | >142Z | A |

TABLE 3-continued

| No. | MOLSTRUCTURE | MW | MS (M + H) | MP | activity class |
|---|---|---|---|---|---|
| 5-24 | 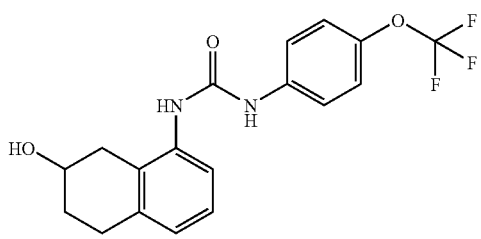 | 314.363 | 315 | >197Z | A |

Example 5-1

N-(7-hydroxy-5,6,7,8-tetrahydro-naphthalen-1-yl)-N'-(4-trifluoromethoxy-phenyl)-urea

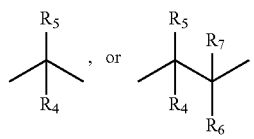

This example was performed according to the general method B.

A mixture of 8-amino-1,2,3,4tetrahydro-naphthalen-2-ol (32.6 mg, 0.20 mmol) and (4trifluoromethoxy-phenyl)-carbamic acid phenyl ester (59.5 mg, 0.20 mmol) in DMSO (1.0 ml) was stirred at 100° C. for 1.5 hours. The mixture-was concentrated under reduced pressure, and then purified by preparatory HPLC to obtain N-(7-hydroxy-5,6,7,8-tetrahydro-naphthalen-1-yl)-N'-(4-trifluoromethoxy-phenyl)-urea (15.5 mg, 21% yield).

$^1$H NMR (DMSO-d6) δ 1.61 (m, 1H),1.87 (m, 1H), 2.40 (m, 1H), 2.85 (m, 2H), 3.96 (m, 1H), 4.88 (d, J=4.2 Hz, 1H), 6.80 (d, J=7.2 Hz, 1H), 7.05 (t, J=7.2 Hz, 1H), 7.28 (d, J=8.7 Hz, 2H), 7.55 (d, J=9.3 Hz, 2H), 7.63 (d, J=7.2 Hz, 1H), 7.85 (s, 1H), 9.24.(s, 1H).

Molecular weight: 366.34
MS (M+H): 367
mp: 198-200 ° C.
In vitro activity class: A.

In a similar method according to the Example 5-1 above, the compounds in Example 5-2 to 5-24 were synthesized.

The invention claimed is:

1. A hydroxy-tetrahydro-naphthalenylurea derivative of the formula (I), its tautomeric or stereoisomeric form, or a pharmaceutically acceptable salt thereof:

(I)

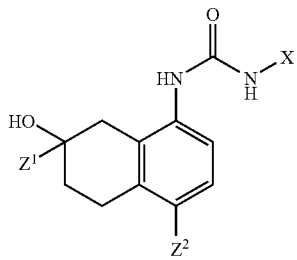

wherein
X represents $C_{1-6}$ alkyl,

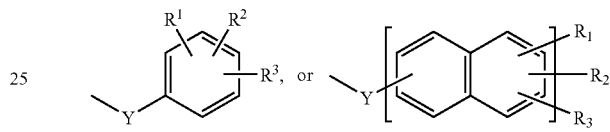

in which
Y represents a direct bond,

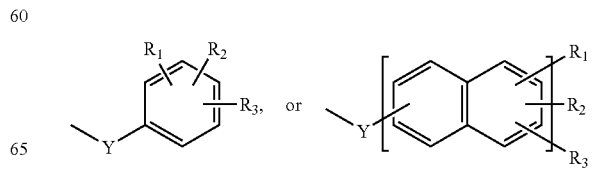

$R^1$, $R^2$ and $R^3$ independently represent hydrogen, halogen, hydroxy, nitro, carboxy, amino, $C_{1-6}$ alkylamino, di($C_{1-6}$ alkyl)amino, $C_{3-8}$ cycloalkylamino, $C_{1-6}$ alkoxycarbonyl phenyl, benzyl, sulfonamide, $C_{1-6}$ alkanoyl, $C_{1-6}$ alkanoylamino, carbamoyl, $C_{1-6}$ alkylcarbamoyl, cyano, $C_{1-6}$ alkyl optionally substituted by cyano, $C_{1-6}$ alkoxycarbonyl or-mono-, di-, or tri-halogen, $C_{1-6}$ alkoxy optionally substituted by mono-, di-, or tri-halogen, phenoxy optionally substituted by halogen or $C_{1-6}$ alkyl, or $C_{1-6}$ alkylthio optionally substituted by mono-, di-, or tri-halogen;

$R^4$, $R^5$, $R^6$ and $R^7$ independently represent hydrogen, $C_{1-6}$ alkyl or phenyl;

$Z^1$ represents hydrogen or $C_{1-6}$ alkyl; and
$Z^2$ represents hydrogen, halogen or $C_{1-6}$ alkyl.

2. The hydroxy-tetrahydro-naphthalenylurea derivative of the formula (I), its tautomeric or stereoisomeric form, or a pharmaceutically acceptable salt thereof as claimed in claim 1, wherein X represents in which
Y represents a direct bond, or

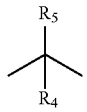

R¹, R² and R³ independently represent hydrogen, halogen, hydroxy, nitro, carboxyl, amino, $C_{1-6}$ alkylamino, di($C_{1-6}$ alkyl)amino, $C_{3-8}$ cycloalkylamino, $C_{1-6}$ alkoxycarbonyl, phenyl, benzyl, sulfonamide, $C_{1-6}$ alkanoyl, $C_{1-6}$ alkanoylamino, carbamoyl, $C_{1-6}$ alkylcarbamoyl, cyano, $C_{1-6}$ alkyl optionally substituted by cyano, $C_{1-6}$ alkoxycarbonyl or mono-, di-, or tri-halogen, $C_{1-6}$ alkoxy optionally substituted by mono-, di-, or tri-halogen, phenoxy optionally substituted by halogen or $C_{1-6}$ alkyl, or $C_{1-6}$ alkylthio optionally substituted by mono-, di-, or tri-halogen;

R⁴ and R⁵ independently represent hydrogen or $C_{1-6}$ alkyl; and $Z^1$ and $Z^2$ each represent hydrogen.

3. The hydroxy-tetrahydro-naphthalenylurea derivative of the formula (I), its tautomeric or stereoisomeric form, or a pharmaceutically acceptable salt thereof as claimed in claim 1, wherein X represents

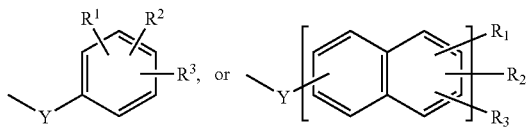

in which
Y represents a direct bond or

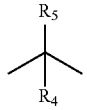

R¹, R² and R³ independently represent hydrogen, halogen, di($C_{1-6}$ alkyl)amino, $C_{3-8}$ cycloalkylamino, $C_{1-6}$ alkoxycarbonyl, $C_{1-6}$ alkyl optionally substituted by cyano, $C_{1-6}$ alkoxycarbonyl or mono-, di-, or tri-halogen, $C_{1-6}$ alkoxy optionally substituted by mono-, di-, or tri-halogen, phenoxy optionally substituted by halogen or $C_{1-6}$ alkyl, or $C_{1-6}$ alkylthio optionally substituted by mono-, di-, or tri-halogen;

R⁴ and R⁵ each represent hydrogen; and $Z^1$ and $Z^2$ each represent hydrogen.

4. The hydroxy-tetrahydro-naphthalenylurea derivative of the formula (I), its tautomeric or stereoisomeric form, or a pharmaceutically acceptable salt thereof as claimed in claim 1, wherein X represents

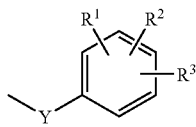

in which
Y represents a direct bond or

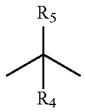

in which
R¹ and R² independently represent hydrogen, chloro, bromo, fluoro, cyclopentylamino, trifluoromethyl, or trifluoromethoxy;
R³, R⁴ and R⁵ each represent hydrogen; and
$Z^1$ and $Z^2$ each represent hydrogen.

5. The hydroxy-tetrahydro-naphthalenylurea derivative of the formula (I), its tautomeric or stereoisomeric form, or a pharmaceutically acceptable salt thereof as claimed in claims 1, wherein
X represents

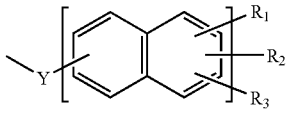

in which
Y represents a direct bond or

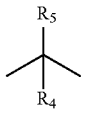

in which
R¹ and R² independently represent hydrogen, chloro, bromo, fluoro, cyclopentylamino, trifluoromethyl, or trifluoromethoxy;
R³, R⁴ and R⁵ each represent hydrogen; and
$Z^1$ and $Z^2$ each represent hydrogen.

6. A hydroxy-tetrahydro-naphthalenylurea derivative of the formula (I), its tautomeric or stereoisomeric form, or a pharmaceutically acceptable salt thereof as claimed in claim 1, wherein said hydroxy-tetrahydro-naphthalenylurea derivative of the formula (I) is selected from the group consisting of:

N-[4-chloro-3-(trifluoromethyl)phenyl]-N'-(7-hydroxy-5,6,7,8-tetrahydro-1-naphthalenyl)urea;
N-(3-chlorophenyl)-N'-(7-hydroxy-5,6,7,8-tetrahydro-1-naphthalenyl)urea;
N-(7-hydroxy-5,6,7,8-tetrahydro-1-naphthalenyl)-N'-[3-(trifluoromethyl)-phenyl]urea;
N-(7-hydroxy-5,6,7,8-tetrahydro-1-naphthalenyl)-N'-[4(trifluoromethyl)-phenyl]urea;
Ethyl 3-({[(7-hydroxy-5,6,7,8-tetrahydro-1-naphthalenyl)amino]carbonyl}-amino)benzoate;
N-(7-hydroxy-5,6,7,8-tetrahydro-1-naphthalenyl)-N'-(1-naphthyl)urea;
N-(7-hydroxy-5,6,7,8-tetrahydro-1-naphthalenyl)-N'-(2-naphthyl)urea;
N-(3,4dichlorophenyl)-N'-(7-hydroxy-5,6,7,8-tetrahydro-1-naphthalenyl)-urea;
N-(7-hydroxy-5,6,7,8-tetrahydro-1-naphthalenyl)-N'-(4isopropylphenyl)urea;

N-(7-hydroxy-5,6,7,8-tetrahydro-1-naphthalenyl)-N'-(4-phenoxyphenyl)urea;
N-[4-chloro-3-(trifluoromethyl)phenyl]-N'-[(7-hydroxy-5,6,7,8-tetrahydro-1-naphthalenyl]urea;
N-(7-hydroxy-5,6,7,8-tetrahydro-1-naphthalenyl)-N'-phenylurea;
N-(4-chlorophenyl)-N'-(7-hydroxy-5,6,7,8-tetrahydro-1-naphthalenyl)urea;
N-(7-hydroxy-5,6,7,8-tetrahydro-1-naphthalenyl)-N'-[2-(trifluoromethyl)-phenyl]urea;
N-(7-hydroxy-5,6,7,8-tetrahydro-1-naphthalenyl)-N'-[4-(trifluoromethyl)-phenyl]urea;
N-(3,4-dichlorophenyl)-N'-(7-hydroxy-5,6,7,8-tetrahydro-1-naphthalenyl)-urea;
N-(7-hydroxy-5,6,7,8-tetrahydro-1-naphthalenyl)-N'-[4-(trifluoromethoxy)-phenyl]urea;
N-(7-hydroxy-5,6,7,8-tetrahydro-1-naphthalenyl)-N'-[4-(trifluoromethoxy)-benzyl]urea;
N-(7-hydroxy-5,6,7,8-tetrahydro-1-naphthalenyl)-N'-(2,4,6-trimethoxybenzyl)urea;
N-(2,6-difluorobenzyl)-N'-(7-hydroxy-5,6,7,8-tetrahydro-1-naphthalenyl)-urea;
N-(7-hydroxy-5,6,7,8-tetrahydro-1-naphthalenyl)-N'-[4-(trifluoromethyl)-benzyl]urea;
N-(7-hydroxy-5,6,7,8-tetrahydro-1-naphthalenyl)-N'-[4-(trifluoromethoxy)-benzyl]urea;
N-[2-(4-chlorophenyl)ethyl]-N'-(7-hydroxy-5,6,7,8-tetrahydro-1-naphthalenyl)urea;
N-[3-fluoro-4-(trifluoromethyl)benzyl]-N'-(7-hydroxy-5,6,7,8-tetrahydro-1-naphthalenyl)urea;
a tautomeric or steroisomeric form of any of the foregoing compounds; and
a pharmaceutically acceptable salt of any of the foregoing compounds.

7. A hydroxy-tetrahydro-naphthalenylurea derivative selected from the group consisting of:
N-[4-chloro-3-(trifluoromethyl)phenyl]-N'-[(7S)-7-hydroxy-5,6,7,8-tetrahydro-1-naphthalenyl]urea;
N-[4-chloro-3-(trifluoromethyl)phenyl]-N'-[(7R)-7-hydroxy-5,6,7,8-tetrahydro-1-naphthalenyl]urea;
N-[(7R)-7-hydroxy-5,6,7,8-tetrahydro-1-naphthalenyl]-N'-[4-(trifluoromethyl)benzyl]urea;
N-[(7S)-7-hydroxy-5,6,1,8-tetrahydro-1-naphthalenyl]-N'-[4-(trifluoromethyl)benzyl]urea;
N-[(7R)-7-hydroxy 5,6,7,8-tetrahydro-1-naphthalenyl]-N'-[4-(trifluoro-methoxy)benzyl]urea;
N-[(7S)-7-hydroxy-5,6,7,8-tetrahydro-1-naphthalenyl]-N'-[4-(trifluoro-methoxy)benzyl]urea; and
a tautomeric or steroisomeric form of any of the foregoing compounds; and
a pharmaceutically acceptable salt of any of the foregoing compounds.

8. A medicament comprising hydroxy-tetrahydro-naphthalenylurea derivative of the formula (I), its tautomeric or stereoisomeric form, or a pharmaceutically acceptable salt thereof as claimed in claim 1 as an active ingredient.

9. The medicament as claimed, in claim 8, further comprising one or more pharmaceutically acceptable excipients.

10. A method of treating a urological disorder or disease mediated in a human or animal by VR1 comprising administering to the human or animal a VR1 antagonistically effective amount of at least one compound according to claim 1.

11. A method of treating pain mediated in a human or animal by VR1 comprising administering to the human or animal a VR1 antagonistically effective amount of at least one compound according to claim 1.

12. A method of treating a urological disorder or disease in a human or animal comprising administering to the human or animal an effective amount of at least one compound according to claim 1, wherein the urological disorder or disease is selected from the group consisting of urge urinary incontinence and overactive bladder.

13. The method of claim 10, wherein the compound is selected from the group consisting of:
N-[4-chloro-3-trifluromethyl)phenyl]-N'-(7-hydroxy-5,6,7,8-tetrahydro-1-naphthalenyl)urea;
N-(3-chlorophenyl)-N'-(7-hydroxy-5,6,7,8-tetrahydro-1-naphthalenyl)urea;
N-7-hydroxy-5,6,7,8-tetrahydro-1-naphtalenyl)-N'-[3-(trifluoromethyl)-phenyl]urea;
N-7-hydroxy-5,6,7,8-tetrahydro-1-naphtalenyl)-N'-[4-(trifluoromethyl)-phenyl]urea;
Ethyl 3-({[(7-hydroxy-5,6,7,8-tetrahydro-1-naphthalenyl)amino]carbonyl}-amino)benzoate;
N-(7-hydroxy-5,6,7,8-tetrahydro-1-naphthalenyl)-N'-(1-napthyl)urea;
N-(7-hydroxy-5,6,7,8-tetrahydro-1-naphthalenyl)-N'-(2-napthyl)urea;
N-(3,4-dichlorophenyl)-N'-(7-hydroxy-5,6,7,8-tetrahydro-1naphtaleny)-urea;
N-(7-hydroxy-5,6,7,8tetrahydro-1-naphthalenyl)-N'-(4-isopropylphenyl)urea;
N-(7-hydroxy-5,6,7,8tetrahydro-1-naphthalenyl)-N'-(4-phenoxyphenyl)urea;
N-[4-chloro-3-trifluoromethyl)phenyl]-N'-[(7-hydroxy-5,6,7,8tetrahydro-1-naphthalenyl]urea;
N-(7-hydroxy-5,6,7,8tetrahydro-1-naphthalenyl)-N'-phenylurea;
N-(4-chlorophenyl)-N'-(7-hydroxy-5,6,7,8tetrahydro-1-naphthalenyl)urea;
N-(7-hydroxy-5,6,7,8tetrahydro-1-naphthalenyl)-N'-[2-(trifluoromethyl)-phenyl]urea;
N-(7-hydroxy-5,6,7,8,-tetrahydro-1-naphthalenyl)-N'-[4-(trifluoromethyl)-phenyl]urea;
N-(3,4-dichlorophenyl)-N'-(7-hydroxy-5,6,7,8-tetrahydro-1-naphthalenyl)-urea;
N-(7-hydroxy-5,6,7,8-tetrahydro-1-naphthalenyl)-N'-[4-(trifluoromethoxy)-phenyl]urea;
N-(7-hydroxy-5,6,7,8-tetrahydro-1-naphthalenyl)-N'-[4-(trifluoromethoxy)-benzyl]urea;
N-(7-hydroxy-5,6,7,8-tetrahydro-1-naphthalenyl)-N'-(2,4,6-trimethoxy-benzyl)urea;
N-(2,6-difluorobenzyl)-N'-(7-hydroxy-5,6,7,8-tetrahydro-1-naphthalenyl)-urea;
N-(7-hydroxy-5,6,7,8-tetrahydro-1-naphthalenyl)-N'-[4-(trifluoromethyl)-benzyl]urea;
N-(7-hydroxy-5,6,7,8-tetrahydro-1-naphthalenyl)-N'-[4-(trifluoromethoxy)-benzyl]urea;
N-[2-(4-chlorophenyl)ethyl]-N'-(7-hydroxy-5,6,7,8-tetrahydro-1-naphthalenyl)urea;
N-[3-fluoro-4-(trifluoromethyl)benzyl]-N'-(7-hydroxy-5,6,7,8-tetrahydro-1-naphthalenyl)urea; and
a tautomeric or stereoisomeric form of any of the foregoing compounds; and
a pharmaceutically acceptable salt of any of the foregoing compounds.

14. A method of treating pain comprising administering to the human or animal an effective amount of at least one compound according to claim 1, wherein the pain is selected from the group consisting of chronic pain, neuropathic pain, postoperative pain, rheumatoid arthritic pain, musculoskeletal pain, back pain, orofascial pain, headache, visceral pain, pelvic pain, vulvodynia, orchialgia and prostatodynia.

15. The method of claim 11, wherein the pain is pain related to a disease or disorder.

16. A method of treating pain related to a disease or disorder comprising administering to the human or animal an effective amount of at least one compound according to claim 1, wherein the disease or disorder is selected from the group consisting of neuralgia, neuropathies, algesia, nerve injury, ischaemia, neurodegeneration, stroke, arthritis, cancer, irritable bowel syndrome and inflammatory lesions of joints, skin, muscles and nerves.

17. The method of claim 11, wherein the compound is selected from the group consisting of

- N-[4-chloro-3-(trifluoromethyl)phenyl]-N'-(7-hydroxy-5, 6,7,8-tetrahydro-1-naphthalenyl)urea;
- N-(3-chlorophenyl)-N'-(7-hydroxy-5,6,7,8-tetrahydro-1-naphthalenyl)urea;
- N-7-hydroxy-5,6,7,8-tetrahydro-1-naphthalenyl)-N'-[3-(trifluoromethyl)-phenyl]urea;
- N-(7-hydroxy-5,6,7,8-tetrahydro-1-naphthalenyl)-N'-[4-(trifluoromethyl)-phenyl]urea;
- Ethyl 3-({[(7-hydroxy-5,6,7,8-tetrahydro-1-naphthalenyl)amino]carbonyl}-amino)benzoate;
- N-(7-hydroxy-5,6,7,8-tetrahydro-1-naphthalenyl)-N'-(1-naphthyl)urea;
- N-(7-hydroxy-5,6,7,8-tetrahydro-1-naphthalenyl)-N'-(2-naphthyl)urea;
- N-(3,4-dichlorophenyl)-N'-(7-hydroxy-5,6,7,8-tetrahydro-1-naphthalenyl)-urea;
- N-(7-hydroxy-5,6,7,8-tetrahydro-1-naphthalenyl)-N'-(4-isopropylphenyl)urea;
- N-(7-hydroxy-5,6,7,8-tetrahydro-1-naphthalenyl-N'-(4-phenoxyphenyl)urea;
- N-[4-chloro-3-(trifluoromethyl)phenyl]-N'-[(7-hydroxy-5,6,7,8-tetrahydro-1-naphthalenyl]urea;
- N-(7-hydroxy-5,6,7,8-tetrahydro-1-naphthalenyl)-N'-phenylurea;
- N-(4-chlorophenyl)-N'-(7-hydroxy-5,6,7,8-tetrahydro-1-naphthalenyl)urea;
- N-(7-hydroxy-5,6,7,8-tetrahydro-1-naphthalenyl)-N'-[2-(trifluoromethyl)-phenyl]urea;
- N-(7-hydroxy-5,6,7,8,-tetrahydro-1-naphthalenyl)-N'-[4-(trifluoromethyl)-phenyl]urea;
- N-(3,4-dichlorophenyl)-N'-(7-hydroxy-5,6,7,8-tetrahydro-1-naphthalenyl)-urea;
- N-(7-hydroxy-5,6,7,8-tetrahydro-1-naphthalenyl)-N'-[4-(trifluoromethoxy)-phenyl]urea;
- N-(7-hydroxy-5,6,7,8-tetrahydro-1-naphthalenyl)-N'-[4-(trifluoromethoxy)-benzyl]urea;
- N-(7-hydroxy-5,6,7,8-tetrahydro-1-naphthalenyl)-N'-(2,4,6-trimethoxy-benzyl)urea;
- N-(2,6-difluorobenzyl)-N'-(7-hydroxy-5,6,7,8-tetrahydro-1-naphthalenyl)-urea;
- N-(7-hydroxy-5,6,7,8-tetrahydro-1-naphthalenyl)-N'-[4-(trifluoromethyl)-benzyl]urea;
- N-(7-hydroxy-5,6,7,8-tetrahydro-1-naphthalenyl)-N'-[4-(trifluoromethoxy)-benzyl]urea;
- N-[2-(4-chlorophenyl)ethyl]-N'-(7-hydroxy-5,6,7,8-tetrahydro-1-naphthalenyl)urea;
- N-[3-fluoro-4-(trifluoromethyl)benzyl]-N'-(7-hydroxy-5,6,7,8-tetrahydro-1-naphthalenyl)urea; and
- a tautomeric or stereoisomeric form of any of the foregoing compounds; and
- a pharmaceutically acceptable salt of any of the foregoing compounds.

18. A method of treating an inflammatory disorder or disease in a human or animal comprising administering to the human or animal an effective amount of at least one compound according to claim 1, wherein the inflammatory disorder or disease is selected from asthma and COPD.

19. The method of claim 18, wherein the compound is selected from the group consisting of:

- N-[4-chloro-3-(trifluoromethyl)phenyl]-N'-(7-hydroxy-5,6,7,8-tetrahydro-1-naphthalenyl)urea;
- N-(3-chlorophenyl)-N'-(7-hydroxy-5,6,7,8-tetrahydro-1-naphthalenyl)urea;
- N-7-hydroxy-5,6,7,8-tetrahydro-1-naphthalenyl)-N'-[3-(trifluoromethyl)-phenyl]urea;
- N-(7-hydroxy-5,6,7,8-tetrahydro-1-naphthalenyl)-N'-[4-(trifluoromethyl)-phenyl]urea;
- Ethyl 3-({[(7-hydroxy-5,6,7,8-tetrahydro-1-naphthalenyl)amino]carbonyl}-amino)benzoate;
- N-(7-hydroxy-5,6,7,8-tetrahydro-1-naphthalenyl)-N'-(1-naphthyl)urea;
- N-(7-hydroxy-5,6,7,8-tetrahydro-1-naphthalenyl)-N'-(2-naphthyl)urea;
- N-(3,4-dichlorophenyl)-N'-(7-hydroxy-5,6,7,8-tetrahydro-1-naphthalenyl)-urea;
- N-(7-hydroxy-5,6,7,8-tetrahydro-1-naphthalenyl)-N'-(4-isopropylphenyl)urea;
- N-(7-hydroxy-5,6,7,8-tetrahydro-1-naphthalenyl-N'-(4-phenoxyphenyl)urea;
- N-[4-chloro-3-(trifluoromethyl)phenyl]-N'-[(7-hydroxy-5,6,7,8-tetrahydro-1-naphthalenyl]urea;
- N-(7-hydroxy-5,6,7,8-tetrahydro-1-naphthalenyl)-N'-phenylurea;
- N-(4-chlorophenyl)-N'-(7-hydroxy-5,6,7,8-tetrahydro-1-naphthalenyl)urea;
- N-(7-hydroxy-5,6,7,8-tetrahydro-1-naphthalenyl)-N'-[2-(trifluoromethyl)-phenyl]urea;
- N-(7-hydroxy-5,6,7,8,-tetrahydro-1-naphthalenyl)-N'-[4-(trifluoromethyl)-phenyl]urea;
- N-(3,4-dichlorophenyl)-N'-(7-hydroxy-5,6,7,8-tetrahydro-1-naphthalenyl)-urea;
- N-(7-hydroxy-5,6,7,8-tetrahydro-1-naphthalenyl)-N'-[4-(trifluoromethoxy)-phenyl]urea;
- N-(7-hydroxy-5,6,7,8-tetrahydro-1-naphthalenyl)-N'-[4-(trifluoromethoxy)-benzyl]urea;
- N-(7-hydroxy-5,6,7,8-tetrahydro-1-naphthalenyl)-N'-(2,4,6-trimethoxy-benzyl)-urea;
- N-(2,6-difluorobenzyl)-N'-(7-hydroxy-5,6,7,8-tetrahydro-1-naphthalenyl)-urea;
- N-(7-hydroxy-5,6,7,8-tetrahydro-1-naphthalenyl)-N'-[4-(trifluoromethyl)-benzyl]urea;
- N-(7-hydroxy-5,6,7,8-tetrahydro-1naphthalenyl)-N'-[4-(trifluoromethoxy)-benzyl]urea;
- N-[2-(4-chlorophenyl)ethyl]-N'-(7-hydroxy-5,6,7,8-tetrahydro-1-naphthalenyl)urea;
- N-[3-fluoro-4-(trifluoromethyl)benzyl]-N'-(7-hydroxy-5,6,7,8-tetrahydro-1-naphthalenyl)urea;
- a tautomeric of stereoisomeric form of any of the foregoing compounds; and
- a pharmaceutically acceptable salt of any of the foregoing compounds.

* * * * *

UNITED STATES PATENT AND TRADEMARK OFFICE
CERTIFICATE OF CORRECTION

PATENT NO. : 7,612,113 B2
APPLICATION NO. : 10/513848
DATED : November 3, 2009
INVENTOR(S) : Yura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 794 days.

Signed and Sealed this

Nineteenth Day of October, 2010

David J. Kappos
*Director of the United States Patent and Trademark Office*